US007189691B2

(12) United States Patent
Hemenway

(10) Patent No.: US 7,189,691 B2
(45) Date of Patent: Mar. 13, 2007

(54) METHODS AND COMPOSITIONS FOR TREATING LEUKEMIA

(75) Inventor: Charles S. Hemenway, New Orleans, LA (US)

(73) Assignee: The Administrators of the Tulane Educational Fund, New Orleans, LA (US)

( * ) Notice: Subject to any disclaimer, the term of this patent is extended or adjusted under 35 U.S.C. 154(b) by 0 days.

(21) Appl. No.: 11/094,595

(22) Filed: Mar. 31, 2005

(65) Prior Publication Data

US 2005/0222012 A1 Oct. 6, 2005

Related U.S. Application Data

(60) Provisional application No. 60/558,456, filed on Apr. 1, 2004.

(51) Int. Cl.
*A61K 38/03* (2006.01)
(52) U.S. Cl. .......................................... 514/2; 530/300
(58) Field of Classification Search ..................... None
See application file for complete search history.

(56) References Cited

U.S. PATENT DOCUMENTS 6,475,753 B1 * 11/2002 Ruben et al. .............. 435/69.1

OTHER PUBLICATIONS

Ayton et al., "Molecular mechanisms of leukemogenesis mediated by MLL fusion proteins", *Oncogene* Sep. 10, 2001 20(40):5695-5707.
Biondi et al., "Biological and therapeutic aspects of infant leukemia", *Blood* Jul. 1, 2000 96(1):24-33.
Chessells et al., "Clinical features, cytogenetics and outcome in acute lymphoblastic and myeloid leukaemia of infancy: report from the MRC Childhood Leukaemia working party", *Leukemia* May 2002 16(5):776-784.
Collins et al., "Mouse Af9 is a controller of embryo patterning, like Mll, whose human homologue fuses with Af9 after chromosomal translocation in leukemia", *Mol. Cell. Biol.* Oct. 2002 22(20):7313-7324.
Corral et al., "An Mll-AF9 fusion gene made by homologous recombination causes acute leukemia in chimeric mice: a method to create fusion oncogenes", *Cell* Jun. 14, 1996 85(6):853-861.
Dimartino et al., "A carboxy-terminal domain of ELL is required and sufficient for immortalization of myeloid progenitors by MLL-ELL", *Blood* Dec. 1, 2000 6(12):3887-3893.
Doty et al., "The leukemia-associated gene Ml1tl/ENL: characterization of a murine homolog and demonstration of an essential role in embryonic development", *Blood Cells Mol. Dis.* May-Jun. 2002 28(3):407-417.
Erfurth et al., "MLL fusion partners AF4 and AF9 interact at subnuclear foci", *Leukemia* Jan. 2004 18(1):92-102.
Felix et al., "Leukemia in infants", *Oncologist* Jun. 1999 4(3):225-240.

Felix et al., "Pediatric Acute Lymphoblastic Leukemia: Challenges and Controversies in 2000", *Hematology* 2000 285-302.
Hess et al., "Defects in yolk sac hematopoiesis in Mll-null embryos", *Blood* Sep. 1, 1997 90(5):1799-1806.
Isnard et al., "Altered lymphoid development in mice deficient for the mAF4 proto-oncogene", *Blood* Jul. 15, 2000 96(2):705-710.
Lavau et al., "Immortalization and leukemic transformation of a myelomonocytic precursor by retrovirally transduced HRX-ENL", *EMBO J.* Jul. 16, 1997 16(14):4226-4237.
Lavau et al., "Retrovirus-mediated gene transfer of MLL-ELL transforms primary myeloid progenitors and causes acute myeloid leukemias in mice", *Proc. Natl. Acad. Sci. USA* Sep. 26, 2000 97(20):10984-10989.
Li et al., "AF4 encodes a ubiquitous protein that in both native and MLL-AF4 fusion types localizes to subnuclear compartments", *Blood* Nov. 15, 1998 92(10):3841-3847.
Milne et al., "MLL targets SET domain methyltransferase activity to Hox gene promoters", *Mol. Cell.* Nov. 2002 10(5):1107-1117.
Mitelman, "Recurrent chromosome aberrations in cancer", *Mutat. Res.* Apr. 2000 462(2-3):247-253.
Pui et al., "Clinical heterogeneity in childhood acute lymphoblastic leukemia with 11q23 rearrangements", *Leukemia* Apr. 2003 17(4):700-706.
Pui et al., "Outcome of treatment in childhood acute lymphoblastic leukaemia with rearrangements of the 11q23 chromosomal region", *Lancet* Jun. 1, 2002 359(9321):1909-1915.
Reaman et al., "Treatment outcome and prognostic factors for infants with acute lymphoblastic leukemia treated on two consecutive trials of the Children's Cancer Group", *J. Clin. Oncol.* Feb. 1999 17(2):445-455.
Rowley, "The critical role of chromosome translocations in human leukemias", *Ann. Rev. Genet.* 1998 32:495-519.
Slany et al., "The oncogenic capacity of HRX-ENL requires the transcriptional transactivation activity of ENL and the DNA binding motifs of HRX", *Mol. Cell. Biol.* Jan. 1998 18(1):122-129.
So et al., "Common mechanism for oncogenic activation of MLL by forkhead family proteins", *Blood* Jan. 15, 2003 101(2):633-639.
Yu et al., "Altered Hox expression and segmental identity in Mll-mutant mice", *Nature* Nov. 30, 1995 378(6556):505-508.
Yu et al., "MLL, a mammalian trithorax-group gene, function as a transcriptional maintenance factor in morphogenesis", *Proc. Natl. Acad. Sci. USA* Sep. 1, 1998 (18):10632-10636.
Zeisig et al., "Transcriptional activation is a key function encoded by MLL fusion partners", *Leukemia* Feb. 2003 17(2):359-365.

* cited by examiner

*Primary Examiner*—Anish Gupta
*Assistant Examiner*—Satyanarayana R. Gudibande
(74) *Attorney, Agent, or Firm*—Howson & Howson LLP

(57) ABSTRACT

A compound of the formula R1-Leu-A2-Val-A4-Ile-A6-Leu-A8-A9-A10-R2 SEQ ID NO: 1 or a pharmaceutically acceptable salt thereof, which disrupts the binding between the AF4 and AF9 proteins in mammalian cells in vitro and in vivo is useful in the treatment, prophylaxsis or diagnosis of various forms of leukemia. Such compounds are also useful in drug development for non-peptide mimics of the compounds of the invention.

16 Claims, 13 Drawing Sheets

SPK4 = KKKKKKKRKVLIVRIDLDLLS

SPK6 =

METHODS AND COMPOSITIONS FOR TREATING LEUKEMIA

CROSS-REFERENCE TO RELATED APPLICATIONS

This application claims the benefit of the priority of U.S. provisional patent application No. 60/558,458 filed Apr. 1, 2004.

STATEMENT REGARDING FEDERALLY SPONSORED RESEARCH OR DEVELOPMENT

This work was supported by the National Institutes of Health, Grant No. CA 78318 and the National Childhood Cancer Foundation, Grant No. CA 13539; Subcontract 8018. The United States government has an interest in this invention.

BACKGROUND OF THE INVENTION

The Mixed Lineage Leukemia (MLL) gene at chromosome band 11q23 is commonly involved in reciprocal translocations detected in acute leukemias. A number of experiments show that the resulting MLL fusion genes directly contribute to leukemogenesis. Among the many known MLL fusion partners, AF4 is relatively common, particularly in acute lymphoblastic leukemia in infants. The AF4 protein interacts with the product of another gene, AF9, which is also fused to MLL in acute leukemias.

Eighty percent of cases of acute lymphoblastic leukemia (ALL) that occur in infants (children less than one year of age) have translocations involving the MLL gene at chromosome 11q23. MLL is an ortholog of the *Drosophila* gene Trithorax. Trithorax and MLL gene products play essential roles in embryogenesis, in part by binding the promoters of HOX genes and maintaining the expression of these genes (Yu, B. D., et al., Nature 1995 378: 505–508; Yu, B. D., et al., Proc Natl Acad Sci USA. 1998 95: 10632–10636; Hess, J. L., et al., Blood 1997 90: 1799–1806; and Milne, T. A., et al., Mol Cell 2002 10: 1107–1117). While MLL is rearranged in the majority of infants with leukemia, translocations involving MLL are encountered in all age groups and are particularly common in secondary leukemias that arise following exposure to epipodophyllotoxin-containing chemotherapy regimens (Rowley, J. D. Annu Rev Genet 1998 32: 495–519).

Remarkably, in acute leukemias characterized by MLL gene rearrangements, a portion of MLL is rejoined to any one of nearly 40 different loci. The rearranged gene is expressed and chimeric MLL proteins have been detected in cells (Li, Q., et al., Blood 1998 92: 3841–3847). MLL "partner" genes are surprisingly heterogeneous, but some of them are known to encode transcription factors or proteins with transcriptional activity. Fusion of transcription factors to MLL has been proposed as one mechanism of triggering leukemia by inappropriately activating crucial developmental genes (Ayton, P. M., and Cleary, M. L. Oncogene 2001 20: 5695–707; So, C. W., and Cleary, M. L. Blood 2003 101: 633–639; and Zeisig, B. B., et al, Leukemia 2003 17: 359–65.).

Regardless of the mechanism, there is compelling data to suggest that the MLL fusion proteins are important in the pathogenesis of the disease. First, different MLL fusion proteins are non-randomly associated with specific subtypes of leukemia (Rowley, cited above; Mitelman, F., Mutat Res 2000 462: 247253). Second, retroviral expression of MLL fusion genes causes leukemic transformation of hematopoietic progenitor cells (Lavau, C., et al., EMBO J 1997 16: 4226–4237; DiMartino, J. F., et al., Blood 2000 96: 3887–3893; and Lavau, C., et al., Proc Natl Acad Sci USA 2000 97: 10984–10989). Third, a chimeric knock-in mouse expressing an MLL-AF9 fusion gene develops acute myeloid leukemia (AML) with the characteristics of MLL-AF9 leukemia that occurs naturally in humans (Corral, J., et al., Cell 1996 85: 853–861).

Despite the large number of MLL fusion genes, in more than 50% of infants with ALL, the leukemic blast cells contain the reciprocal translocation t(4;11)(q21;q23) and are associated with a distinctive $CD10^{31}$ $CD19^+$ ALL phenotype. As a consequence of this t(4;11) translocation, the 5' portion of the MLL gene at 11q23 is fused to the 3' portion of a gene at the 4q21 locus designated AF4. Although less common, the next most frequently encountered translocations in infant ALL are t(11;19)(q23;p13) and t(9;11)(p22;q23) (Felix, C. A., et al., Hematology (Am Soc Hematol Educ Program) 2000 285–302; and Pui, C. H., et al., Leukemia 2003 17: 700–6). In these cases, the ENL and AF9 genes respectively are joined to MLL. ENL and AF9 are structurally related proteins and the 3' portion of the genes that fuse to MLL encode nearly identical amino acid sequences (Slany, R. K., et al., Mol Cell Biol 1998 18: 122–129).

Apart from frequent involvement in acute leukemia when expressed as MLL fusion proteins, the biological functions of AF4, ENL and AF9 are not well understood. Like MLL, mouse gene deletion studies have demonstrated important developmental roles for AF4, AF9 and ENL (Isnard, P., et al., Blood 2000 96: 705–710; Collins, E. C et al., Mol Cell Biol 2002 22: 7313–7324; and Doty, R. T., et al., Blood Cells Mol Dis 2002 28: 407–417). AF4 and AF9 form a stable protein complex in the nucleus and the mutual interaction domains of the two proteins are present within MLL fusion proteins (Erfurth, F., et al., Leukemia 2004 18: 92–102). This observation raises the possibility that AF4 and AF9 function in tandem both in their native states and when expressed as a chimeric MLL protein.

Despite considerable advances in the treatment of acute lymphoblastic leukemia in children, ALL in infants remains a particularly challenging disease. Recent clinical trials have produced outcomes with <50% event free survival after 5 years. The prognosis may be even more limited for the large number of infants with t(4;11) leukemia (Felix, C., and Lange, B. J., Oncologist 1999 4: 225–240; Reaman, G. H., et al., J Clin Oncol 1999 17: 445–455; Biondi, A., et al., Blood 2000 96: 24–33; Chessells, J. M., et al., Leukemia 2002 16: 776784). Current treatments for infant ALL include high dose chemotherapy with or without stem cell transplant and are associated with high morbidity in addition to the possibility of disease relapse. An optimal treatment regimen for these high-risk patients is yet to be identified (Pui, C. H et al., Lancet 2002 359: 1909–1915).

There is a great interest in expanding the range of therapies for infant leukemias and an understanding of the biology of the disease has provided some leads. To date, however, no effective disease-specific agent for the treatment of babies with ALL has been described. Thus, there remains a need in the art for compounds and pharmaceutical compositions and methods useful for treatment, prevention and diagnosis of a variety of leukemias, including infant leukemias and secondary leukemias following chemotherapy.

SUMMARY OF THE INVENTION

In one aspect, the present invention provides compounds of the formula R1-Leu-A2-Val-A4-Ile-A6-Leu-A8-A9-A10-R2 SEQ ID NO: 1 or a pharmaceutically acceptable salt thereof. These peptides disrupt the binding between the AF4 and AF9 proteins in mammalian cells in vitro and in vivo and cause apoptosis in leukemia cells. Such compounds are useful in the treatment, prophylaxis and diagnosis of various leukemias. These compounds are also useful in methods for the screening and development of pharmaceutical compounds that mimic the binding ability of these peptides and are similarly useful in the treatment of leukemias, which require for their propagation the binding between the AF4 and AF9 proteins. A variety of embodiments of compounds of this formula, as well as the definitions for the R and A groups in the SEQ ID NO: 1 formula above, are disclosed in the detailed description. These compounds specifically target leukemic cells with t(4;11) translocations and provide compositions and methods for more effective therapies for this type of acute leukemia, infant leukemias and secondary leukemias following chemotherapy.

In another aspect of the invention, a fragment of the above-identified formula, e.g., R1-A2-Val-A4-Ile-A6-R2 SEQ ID NO: 116 or a pharmaceutically acceptable salt thereof forms a useful compound of this invention.

In still another embodiment, the invention provides a pharmaceutical composition containing one or more of the compounds of the above formula in a pharmaceutically acceptable carrier. This composition can contain other pharmaceutically acceptable components for enhancing the penetration of the compound into a cell and/or for extending its bioavailability and increasing its resistance to enzymatic degradation in vivo.

In still another embodiment, the invention provides a kit containing one or more of the compounds of the above formula, as well as optional components such as suitable pharmaceutically or diagnostically acceptable carriers, penetration enhancers or components for extending bioavailability and increasing its resistance to enzymatic degradation in vivo, fusion peptides, detectable reagents, physical delivery means and other similar items.

In yet another embodiment, the invention provides a method of treating or preventing the development of leukemia in a mammalian subject comprising administering to said subject a composition as described above.

In a further aspect, the invention provides the use of a compound or composition described above in the preparation of a medicament for the treatment or prophylaxsis of leukemia in a mammalian subject.

Still a further aspect of the present invention is a method for designing pharmaceutical compounds. One exemplary method involves employing a compound described above in a computer modeling program to design a compound which mimics the structure and AF4/AF9 binding disruption biological effect thereof. Another exemplary embodiment involves a comparative assay. By exposing a leukemia cell susceptible to apoptosis by contact with a compound of the invention to at least one test compound, one may identify a test compound which produces a similar inhibitory effect upon the binding of AF4/AF9 proteins in the cell line. Such a test compound is thus a likely mimetic of any of the peptide compounds described herein.

Other aspects and advantages of the present invention are described further in the following detailed description of the preferred embodiments thereof.

DETAILED DESCRIPTION OF THE INVENTION

Figure 1:
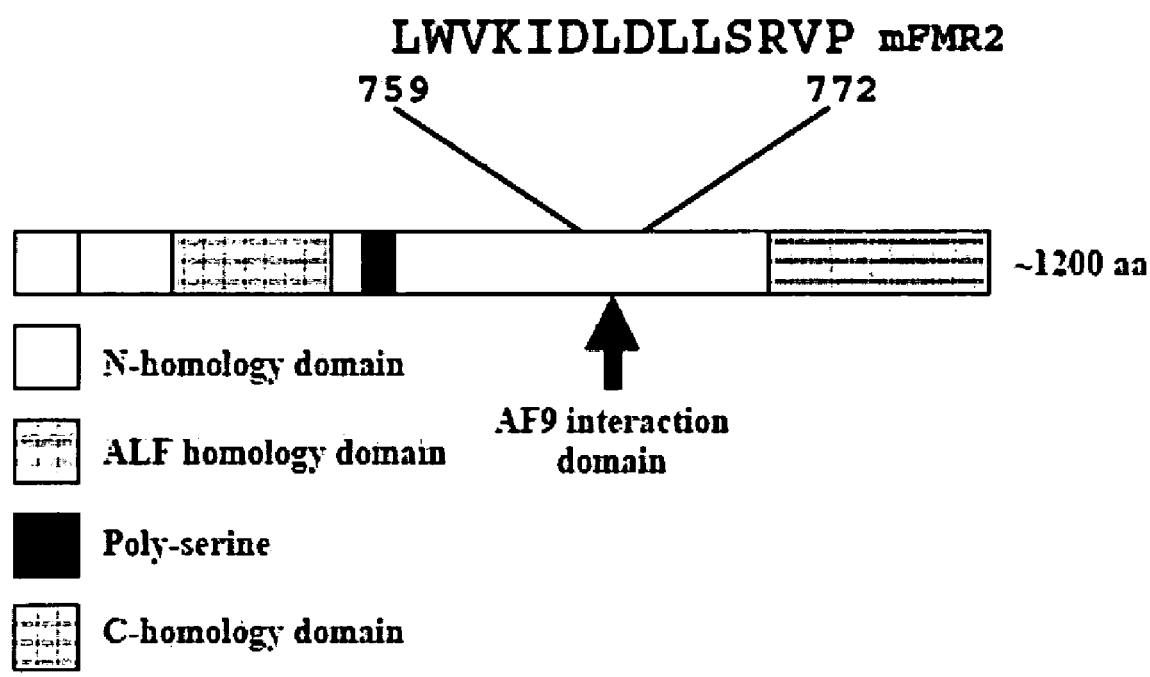
FIG. 1 is a schematic illustrating that the AF9 interaction domain is conserved among the AF4 homologs. The amino acid sequences of the AF9 interaction domains of human and mouse AF4 family members are depicted (SEQ ID NO: 2). The conserved AF9 interaction domain is found within a region of the AF4 family members that is otherwise characterized by sequence heterogeneity. Homologous regions of the proteins are indicated by shading according to the analysis of Ma, C., and Staudt, L. M. Blood 1996 87: 734–745.

The present invention provides compounds and peptides isolated from naturally-occurring proteins as well as modified or derivative compounds thereof, which compounds are designed to disrupt a multiprotein complex comprised of the MLL fusion partners AF4 and AF9. In one embodiment, these compounds and peptides are structurally based on a fragment of the naturally occurring human and murine AF4 protein, AF5 protein and FMR2 proteins. These compounds have activity against multiple leukemia cell lines with MLL gene rearrangements. Specifically, and as exemplified below, cell lines that express MLL-AF4 or the closely related MLL-AF5 fusion genes are most potently inhibited by an exemplary compound of this invention. For ease of discussion, the examples below employ the peptide compound PFWT SEQ ID NO: 2. However, as discussed herein, a wide variety of peptide analogs, as well as peptide mimetics, may be employed for the same purposes. The examples below demonstrate that PFWT has profound effects on the co-localization of fluorescent protein-tagged molecules containing AF9 and AF4. In a subset of leukemias, the interaction between chimeric MLL-AF4 (or MLL-AF5) proteins and AF9 produces an arrest in the differentiation of the cells that contributes to leukemic transformation. Disruption of the interaction of the leukemic oncoproteins by PFWT relieves this differentiation arrest, leading to apoptosis.

The sensitivity of leukemia cell lines with t(4;11) and t(5;11) translocations demonstrates that chimeric MLL proteins are the relevant targets of the peptide. However the results discussed specifically herein permit another possible mechanism of the compounds of this invention, i.e., that PFWT interferes with native protein complexes composed of unaltered AF4 and AF9. Significantly, the PFWT peptide has a significant inhibitory effect on at least one leukemia cell line, Reh, which does not contain a known MLL gene rearrangement. This finding implicates native AF4 and AF9 as targets of the peptide. There are also numerous AF4 and AF9 family members that may also form protein complexes that could be disrupted by PFWT (Domer, P. H., et al Proc Natl Acad Sci USA 1993 90: 7884–7888; Rubnitz, J. E., et al, Blood 1994 84: 1747–1752; Gecz, J et al., Nat Genet 1996 13: 105–108; Gu, Y., et al., Nat. Genet 1996 13, 109–113; and Ma, C., and Staudt, 1996, cited above). However, as demonstrated specifically below and in vitro, PFWT does not interfere with the interaction of AF9 with its other carboxy-terminal binding partners, MPc3 and mBCoR. Therefore, the peptide is specific for protein complexes containing AF4 and AF9 (or their family members) and not for other AF9 binding proteins.

Although PFWT disrupts AF4-AF9 protein interactions, it does not substantially inhibit the THP-1 cell line expressing an MLL-AF9 fusion gene. Recruitment of AF9 by MLL-AF4 oncoproteins is likely required for leukemogenesis, while binding of AF4 to MLL-AF9 is not a prerequisite for the process. AF9 is a crucial mediator of leukemogenesis by recruiting crucial transcription factors to the promoter occupied by the MLL fusion protein. Consistent with this theory of the mechanism of the invention, the AF9 homolog ENL has been identified as a component of the SWI/SNF chromatin-remodeling complex (Nie, Z., et al., Mol Cell Biol 2003 23: 2942–2952). Alternatively, it is possible that THP-1 cells lack intact signaling pathways that trigger apoptosis or have other blocks to apoptosis required for the cytotoxic effect of PFWT. It is also possible that this cell line has other mechanisms of resistance that relate to the disposition of the peptide.

Based on the cytotoxic effect of the peptide drug on leukemia cells containing the t(4;11) translocation, PFWT serves as a model of new chemotherapeutic agents for t(4;11) leukemia, a disease that generally responds poorly to current chemotherapy regimens. Because the therapeutic utility of peptides is often compromised by their sensitivity to proteases and limited intracellular uptake, among other factors, compounds of this invention also contain strategic modifications to increase the stability and bioavailability or increase the ability of the compound to penetrate the cell wall. Also, as described below, PFWT and its derivative peptides serve as reagents to screen small non-peptide molecules that disrupt AF4-AF9 protein complexes but that may possess more favorable pharmacologic properties.

In the following discussion, amino acids may be referred to by their conventional 3 letter designations or, for convenience, by their single letter designations. One of skill in the art is readily able to interpret the intended amino acid residue by either name.

A. Peptides of the Invention

According to this invention, preferred compounds of the present invention are defined by the following formula (hereinafter referred to as "the formula of the invention"):

R1-Leu-A2-Val-A4-Ile-A6-Leu-A8-A9-A10-R2 SEQ ID NO: 1. As used in the above formula and unless otherwise specified in the disclosure below, any, some or all amino acids in the formula may be amino acids that are naturally occurring in mammalian proteins; or they may non-naturally occurring amino acids or mutated amino acids. The amino acids designated by A2, A9 and A10 in the formula are preferably hydrophobic amino acids. The amino acid designated A4 is a positively charged amino acid. The amino acid residues A6 and A8 in the formula may be any amino acid. For example, in various compounds of the above formula A4 is one of the naturally-occurring positively-charged amino acids Lys, Arg or His. Amino acids A6 and A8 may be independently any of the naturally-occurring amino acids, e.g., Ala, Arg, Asn, Asp, Cys, Gln, Glu, Gly, His, Ile, Leu, Lys, Met Phe, Pro, Ser, Thr, Trp, Tyr, and Val. In these and other alternative embodiments, the amino acids A2, A9 and A10 are independently selected from naturally-occurring hydrophobic amino acids Val, Trp, Ile, Leu, Met, Phe, and Tyr.

Further, smaller peptides, which incorporate at least the sequence A2-Val-A4-Ile-A6 SEQ ID NO: 116, and derivatives thereof that contain modifications including one or more of the modifications described herein as applied to the 10-residue peptide, are also useful compounds of the present invention. Such small peptides that have the biological activity to disrupt AF4/AF9 binding may also contain modifications on the amino and/or carboxy termini to increase solubility or prevent aggregation.

However, other embodiments of compounds of this invention employ as one or more of the variable or constant amino acids in the formula above, non-naturally-occurring amino acid. The term "non-naturally-occurring amino acid" as used herein means a derivative or modified amino acid that generally does not occur naturally in mammalian proteins, and specifically in the isolated fragments above. Such non-naturally occurring amino acid(s) when employed in the compounds above are anticipated to make the compounds more resistant to degradation by mammalian enzymes in serum, saliva, stomach and intestines, and thus compounds that are composed of one or more such amino acids may confer upon the compound enhanced stability and bioavailability in vivo. A variety of methods for producing non-natural amino acids are known and may be selected by one of skill in the art.

For example, one class of non-naturally occurring amino acids is L amino acids that effect stereochemistry. Thus in one embodiment of compounds of this invention one or more of the amino acids in the peptide may be in L form, while others may be in D form. Another non-naturally occurring amino acid is an amino acid which is modified to contain a substitution on the alpha-carbon in the amino acid structure. For example the alpha carbon may be substituted by a suitable hydrocarbon moiety, such as aminoisobutyrate. Still another class of non-naturally occurring amino acids are amino acids which are modified or mutated to extend their carbon chain length. For example, an amino acid with a single alpha carbon chain, may be extended with at least one additional carbon, i.e., a beta carbon, and so on. An additional modification to an amino acid is the insertion of a substituent on the nitrogen of the amino group. An example of this type of modification is an N-methyl amino acid. The addition of substituents on the alpha carbon or additional carbons or on the nitrogen of the amino acid molecule may occur in any of the amino acids of the formula above.

Among useful substituents for creating the non-naturally occurring amino acids are a straight chain, branched, cyclic or heterocyclic $C_{1-12}$ alkyl group, and straight chain, branched, cyclic, or heterocyclic $C_{1-12}$ alkanoyl group. The amino acid may be also modified by the insertion of modifying sugars, imide groups and the like. Other amino acids are substituted in the ortho or meta position by a substituent such as H, OH, $CH_3$, halogen, $OCH_3$, $NH_2$, CH or $NO_2$.

In some embodiments of the present invention, the compounds will contain non-naturally-occurring amino acids on the amino or carboxy terminal amino acids of the formula. In other embodiments, one or more such non-naturally occurring amino acid may be placed in the middle amino acids. Other embodiments may have amino acid modifications on the relatively constant amino acids in the above formula.

A non-exclusive list of modified or non-naturally occurring amino acids for inclusion in compounds fitting the formula above include amino acids modified by N-terminal acetylation, C-terminal amidation, formylation of the N-terminal methionine, gamma-carboxyglutamic acid hydroxylation of Asp, Asn, Pro or Lys residues in the compound, methylation of Lys or Arg, preferably; phosphorylation of Ser, Thr, Tyr, Asp or His in the compound, use of a pyrrolidone carboxylic acid, which is an N-terminal glutamate which has formed an internal cyclic lactam, sulfatation of Tyr, generally. Still other modifications of non-naturally occurring amino acids include use of or substitution of the following moieties: a 2-aminoadipic acid group, a 3-aminoadipic acid group, beta-Ala or beta-aminopropionic acid group, 2-aminobutryic acid, 4-aminobutyric acid, piperidinic acid, 6-aminocaproic acid, 2-aminoheptanoic acid, 2-aminoisobutryic acid, 3-aminoisobutyic acid, 2-aminopimelic acid, 2,4 diaminobutyric acid, desmosine, 2,2'-diaminopimelic acid, 2,3-diaminopropionic acid, N-ethylglycine, N-ethylglycine, N-ethyl asparagines, hydroxylysine, allo-hydroxylysine, 3-hydroxyproline, 4-hydroxyproline, isodesmosine, allo-isoleucine, N-methylglycine, sarcosine, N-methylisoleucine, 6-N-methyllysine, N-methylvaline, 6-N-methyllysine, norvaline, norleucine, and ornithine.

Also used in the formula above are other optional N and C-terminal modifications of the peptide compound, i.e., designated R1 and R2. Thus, for example, R1 may be selected from one or more of the following groups: hydrogen, a straight chain, branched, cyclic or heterocyclic alkyl group (preferably $C_{1-12}$); a straight chain, branched, cyclic or heterocyclic alkanoyl group (preferably $C_{2-12}$), a sequence of one to 15 additional naturally occurring or non-naturally occurring, substituted or unsubstituted amino acids; or a spacer compound or sequence capable of cyclizing the peptide by bridging between the N- and C-termini thereof. Other selections for the R1 moiety can include an acidic moiety, and a peptide or protein for fusion, preferably to the N-terminus to enhance penetration or transport of the compound into the cell.

In one embodiment, 1-aminocyclo-hexane carboxylic acid (Chex) is employed as R1. In another embodiment, the R1 group is a penetration enhancer formed by one or more positively charged amino acid residues or amino acid sequences. R1 is alternatively a sequence of amino acids with a net positive charge, such as Arg-Val-, Lys-Val-, Lys-Val-Asp-Lys-Val- SEQ ID NO: 6, and about three to seven repetitions of a single amino acid, e.g., Lys. In still other embodiments, such additional amino acids are modified by an acetyl group, preferably a group that confers a positive charge on the compound N-terminus. Some examples of these R1 groups are Acetyl-Arg-Val-; Acetyl-Lys-Val-; and Acetyl-Lys-Lys-Lys-Lys- SEQ ID NO: 7. The R1 group may be defined as R3-selected amino acid-, wherein R3 is a straight chain, branched, cyclic or heterocyclic $C_{1-12}$ alkyl group, or a straight chain, branched, cyclic or heterocyclic $C_{1-12}$ alkanoyl group. The R1 groups may also employ the above-listed amino acid modifications.

In still other embodiments of peptides falling within the formula of the present invention, the R1 group includes nuclear localization sequences in place or or in addition to penetration enhancers. Such nuclear localization sequences enable targeting of the compound to the nucleus of the target cell, e.g, the SV-40 sequence Arg-Lys-Val. A variety of such sequences can be found in the NLSdb database of nuclear localization signals, accessed via the web site: http://cubic.bioc.columbia.edu/db/NLSdb/.

In still other embodiments of peptides falling within this formula, the R1 group is a reporter group useful for detection purposes. A reporter group may be defined as a moiety which is capable, alone or in concert with other compositions or compounds, of providing a detectable signal. The reporter may be interactive to produce a detectable signal. Most desirably, the reporter is detectable visually, e.g. colorimetrically. A variety of enzyme systems have been described in the art which will operate to reveal a colorimetric signal in an assay. As one example, glucose oxidase (which uses glucose as a substrate) releases peroxide as a product. Peroxidase, which reacts with peroxide and a hydrogen donor such as tetramethyl benzidine (TMB) produces an oxidized TMB that is seen as a blue color. Other reporters include horseradish peroxidase (HRP) or alkaline phosphatase (AP), and hexokinase in conjunction with glucose-6-phosphate dehydrogenase which reacts with ATP, glucose, and NAD+ to yield, among other products, NADH that is detected as increased absorbance at 340 nm wavelength.

Other reporter molecules that may be utilized in the methods of this invention are biotin-avidin, fluorescent compounds such as fluorescein, green and blue fluorescent proteins; and radioactive compounds or elements, such as radioactive iodine, and the like. For example, in some compounds of this invention the R1 group is the reporter biotin bound to an N-terminal amino acid by a covalent bond. Still another peptide of this invention contains an R1 group which is a reporter group covalently bonded to one or more amino acid residues, e.g. a 5(6) carboxyfluorescein functionalized-Lys-. Such reporters for attachment to the N-termini of the peptides of this invention may be readily selected from among numerous compositions known and readily available to one skilled in the art of diagnostic assays. The above-listed reporters are understood to be non-exclusive.

Still other compounds of this invention are cyclic peptides, and in these peptides, R1 is an amino acid "spacer". Spacers are sequences of greater than 3 amino acids which are interposed between the normal N-terminus and C-terminus of the modified compound to create a structural turn. In one embodiment, an amino acid spacer is greater than 5 amino acid residues in length. In a preferred embodiment, the amino acid spacer is greater than 10 amino acid residues in length. The amino acid residues in the spacer may be a sequence of any natural or non-naturally occurring amino acids. One such spacer molecule is Gly-Pro-Ala-Gly. These spacers permit linkage between two peptide sequences without imposing any adverse restraint upon the molecular structure. Spacers may also contain restriction endonuclease cleavage sites to enable separation of the sequences, where desired. Desirably, spacers duplicate at least a portion of the formula above. Suitable spacers or linkers are known and may be readily designed and selected by one of skill in the art.

For example, a cyclic compound of this invention can contain two versions of the sequence Leu-A2-Val-A4-Ile-A6-Leu-A8-A9-A10 SEQ ID NO: 1, in which the A10 of said sequence linked to the N-terminal amino acid or R1 of said formula, and said C-terminal amino acid or R2 of said formula linked to the N-terminal Leu of said sequence. For example, the spacer incorporates a duplicate sequence Leu-Met-Val-Lys-Ile-Thr-Leu-Asp-Leu-Leu SEQ ID NO:8, so that the resulting compound is a dimer in which the R1 or first N-terminal amino acid of the first peptide of the formula is linked via a covalent bond to the R2 or last C-terminal amino acid of the second peptide of the formula and the R2 or last C-terminal amino acid of the first peptide of the formula is linked via a covalent bond to the R1 or first N-terminal amino acid of the second peptide.

Figure 5A:
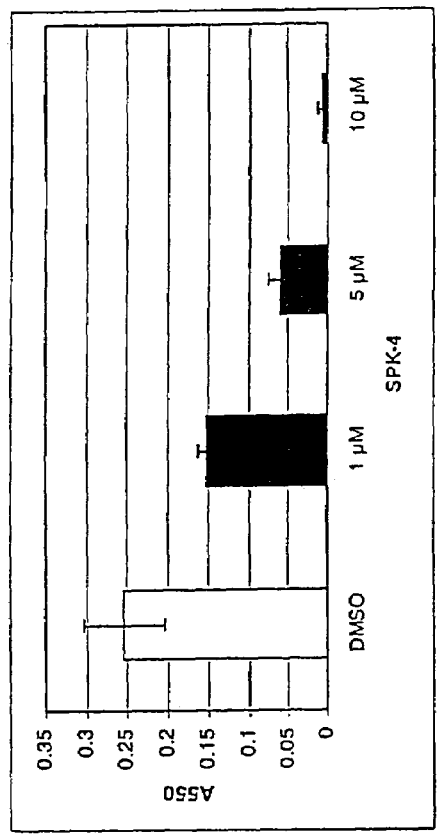
FIG. 5A is a bar graph showing that an exemplary compound SPK4 SEQ ID NO: 5 (which has a polylysine sequence and SV40 nuclear localization signal as R1) inhibits leukemia cell line B1 with t(4;11) and t(5;11) translocations. Cells were treated with the peptide compounds SPK4 (dark bars) at differing concentrations, or vehicle (DMSO; white bar) for 72 h and viability was determined by MTT assay similarly to that described in Example 5.

In another example, a cyclic peptide may be formed in which a compound of the invention, R1-Leu-Leu-Ala-Leu-Ala-Ile-Lys-Val-Ile-Leu-R2 SEQ ID NO: 9 has an R2 spacer Gly-Ala-Pro-Gly (amino acids 11–14 of SEQ ID NO: 4), wherein the second Gly in the spacer is linked to a second repeat of the compound sequence Leu-Leu-Ala-Leu-Ala-Ile-Lys-Val-Ile-Leu SEQ ID NO: 9, and wherein R1 is a hydrocarbon moiety linking the carbon atoms of the N-terminal L of one compound to the C-terminal L of the second compound. The resulting cyclic peptide appears as depicted in FIG. 5.

Where the R1 group is a penetration enhancer or transport sequence, R1 may be selected from among a host of known "cell penetrating peptides" (CPP) or "protein transduction domains" (PTD). Thus, some examples of suitable CPPs are arginine-rich peptides, and more specifically, linear or branched-chain peptides containing approximately 8 residues of arginine (See, e.g., Futaki et al Curr. Prot. Pept. Sci., 2003 4(2):87–96; and Futaki Int. J. Pharm, 2002 245(1–2): 1–7, both incorporated by reference herein). Other suitable CPPs are also discussed in International Published Patent Application Nos. WO 03/035892 and WO 03/035697.

Suitable PTDs include transactivating protein analogs or fragments thereof, such as the HIV-1 Tat (Vives et al, Curr. Protein Pept. Sci., 2003 4(2):125–32). The HIV-1 Tat basic peptide sequence is an example of the prototypic cell membrane-permeant component. U.S. Pat. No. 6,348,185 refers to cell membrane-permeant peptides including peptides of 4 to 6 amino acids derived from HIV-1 Tat, linked to pharmaceutically active substances via a functional linker that confers target cell specificity to the composition. U.S. Pat. Nos. 5,804,604; 5,747,641; 5,674,980; 5,670,617; 5,652,122 (Frankel) refers to the use of Tat peptides to transport covalently linked biologically active cargo molecules into the cytoplasm and nuclei of cells. Morris et al, Nat. Biotechnol., 2001 19(12):1173–76 refers to PTDs including TAT protein sequences. U.S. Pat. No. 5,804,604 refers to Tat-derived transport polypeptides. A commercial useful peptide transport molecule is the CHARIOT™ reagent (Active Motif).

Still other options for the transport moiety useful in the present invention are described in U.S. Pat. Nos. 5,135,736 and 5,169,933 (Anderson), which refer to the use of covalently linked complexes (CLCs) to introduce molecules into cells. CLCs comprise a targeting protein, preferably an antibody, a cytotoxic agent, and an enhancing moiety. Specificity is imparted to the CLC by means of the targeting protein, which binds to the surface of the target cell. After binding, the CLC is taken into the cell by endocytosis and released from the endosome into the cytoplasm. In one embodiment, Anderson refers to the Tat protein as part of the enhancing moiety to promote translocation of the CLC from the endosome to the cytoplasm. The complexes are limited in their specificity to cells that can be identified by cell surface markers. In addition, the attachment of enhancing moieties to the CLC is accomplished by the use of bifunctional linkers. The use of bifunctional linkers results in the production of a heterogeneous population of CLCs with varying numbers of enhancing moieties attached at varying locations.

Yet another embodiment of R1 as a transport moiety is a peptide-oligodeoxynucleotide conjugate described by L. Chaloin et al, *Biochem.*, 1997 37:11179–87. These conjugates comprise the combination of a peptide containing a hydrophobic motif associated with a hydrophilic nuclear localization sequence covalently linked to a small molecule to facilitate the cellular internalization of small molecules. The hydrophobic sequences used correspond to a signal peptide sequence or a fragment of the fusion peptide GP41. One peptide successfully targeted fluorescent oligodeoxynucleotides into living cells (Chaloin et al, Biochem. Biophys. Res. Commun., 1998 243(2):601–608). Still another suitable R1 transport peptide is described by Taylor et al, *Electrophoresis*, 2003 24(9):1331–1337 and refers to an amphipathic peptide Pep-1 which may be used as a transport peptide in combination with a nonionic detergent carrier, for delivery of SDS-PAGE isolated proteins into a cell.

The R1 transport moiety useful in the present invention can be any cell membrane-permeant basic peptide component of the complexes described in the above-cited documents, all of which are incorporated by reference herein. The transport moiety can be a peptide or protein that comprises any amino acid sequence (including naturally-occurring amino acids or non-natural amino acids, such as D amino acids) that confers the desired intracellular translocation and targeting properties to the selected therapeutic peptide or protein. Preferably, these amino acid sequences are characterized by their ability to confer transmembrane translocation and internalization of a complex construct when administered to the external surface of an intact cell. Attachment of a compound of the formula of the present invention to the R1 transport moiety would permit the resulting composition to be localized within cytoplasmic and/or nuclear compartments.

Specific R1 cell membrane-permeant peptide sequences useful in practicing the present invention include, but are not limited to, sequences of the following proteins and fragments and homologous sequences derived therefrom: the HIV-1 Tat protein, the HIV-1 Rev protein basic motif, the HTLV-1 Rex protein basic motif, the third helix of the homeodomain of Antennapedia, a peptide derivable from the heavy chain variable region of an anti-DNA monoclonal antibody, the Herpes simplex virus VP22 protein, the Chariot™ protein, and the Pep-1 protein. The minimum number of amino acid residues can be in the range of from about three to about six, preferably from about three to about five, and most preferably about four.

The R1 group can also contain an enzymatic cleavage site for interposition between the penetration enhancer sequence and the peptide of the above formula. This optional sequence permits the penetration enhancer to be cleaved from the peptide intracellularly, if desired. Selection of such cleavage sites is within the skill of the art.

The R2 group of the above formula of compounds of the present invention may be selected from H, OH, $CO_2H$, $CONH_2$, an imide group, a sugar, a straight chain, branched, cyclic or heterocyclic $C_{1-12}$ alkyl group; a straight chain, branched, cyclic or heterocyclic $C_{1-12}$ alkanoyl group; an amide, imide or sugar substituted with at least one of said alkyl or alkanoyl groups, a sequence of one or up to about 15 additional naturally occurring or non-naturally occurring amino acids, and a spacer capable of cyclizing the compound by bridging between the N- and C-termini thereof. The additional amino acids may also form spacers, as described above for $R^1$, to cyclize the peptide by bridging between the N- and C-termini of the peptide. For example, in some peptides, R2 is D-Asn, L-Asn, Asp, or Asn-R4, wherein R4 is a sugar. In some embodiments R2 is 2-acetamido-2-deoxyglucose; in other preferred embodiments, the R4 is triacetyl 2-acetamido-2-deoxyglucose. In other embodiments of the peptides of this invention R2 is a β-acetyl-2,3-diamino propionic acid group (Dpr(Ac)). The R2 groups may also employ the above-listed amino acid modifications.

As described above, the compounds of this invention include modified peptides in which the amino acids may be connected by conventional amide bonds. Alternatively, modified peptides include those in which one or more of the natural or unnatural amino acids may be connected by bonds resistant to proteases, such as, a thioamide bond or a reduced amide bond. Such modifications of the bonds between amino acids may change the conformation of the compounds. Other backbone-modifications of these compounds are also anticipated to improve proteolytic stability and yield analogs with slightly modified activity spectrum. Preferably, one or more of these compounds is a synthetic peptide fused to a second moiety, which moiety enhances the bioavailability of said peptide.

Figure 5B:
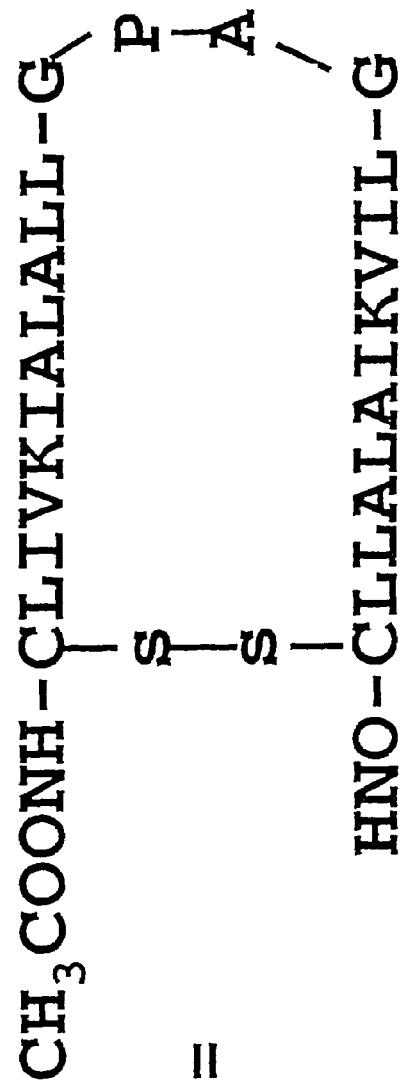
FIG. 5B is a prototype cyclic peptide SPK6 SEQ ID NO: 4, formed by two repeats of a peptide of the formula of this invention (i.e., Leu-Ile-Val-Lys-Ila-Ala-Leu-Ala-Leu-Leu SEQ ID NO: 117) with a 4 amino acid spacer (i.e., Lys-Pro-Ala-Gly SEQ ID NO: 118) which forms a β turn attached at the carboxy terminus of the first peptide and to the amino terminus of the second peptide. At the amino terminus of the first peptide, R1 is an aceylated Cys; at the carboxy terminus of the second peptide R2 is an amidated Cys. The two Cys are attached to each other by a disulfide bond.

Examples of certain preferred embodiment of compounds according to this invention include compounds of the formula recited above in which A2 is preferably Met or Trp. In other embodiments of compounds of the above formula, A6 is preferably Asp or Thr. In some embodiments of compounds of the above formula, R2 is preferably—Ser-Arg-A13-Pro SEQ ID NO: 10, wherein A13 is Ile or Val. In still other preferred embodiments of this invention, R1 is Lys-Lys-Lys-Lys-Lys-Arg-Lys-Val- SEQ ID NO: 11 or Lys-Lys-Arg-Lys-Val- SEQ ID NO: 12. In still other preferred embodiments, the following substitutions are used individually or collectively, for example, A2 is Ile and A4 is Arg, A6 is Asp, A10 is Asp and R2 is Leu-Ser. A specific exemplary compound of the invention, referred to as SPK4 has the sequence Lys-Lys-Lys-Lys-Lys-Lys-Arg-Lys-Val-Leu-Ile-Val-Arg-Ile-Asp-Leu-Asp-Leu-Leu-Ser- SEQ ID NO: 5. In yet another embodiment, A2 is Ile, A6 is Ala, A8 is Ala. A specific exemplary compound of the invention, referred to as SPK6 monomer has the sequence Leu-Ile-Val-Lys-Ile-Ala-Leu-Ala-Leu-Leu SEQ ID NO: 13. A cyclic compound, referred to as SPK6 is a dimer of SEQ ID NO: 4, and is illustrated in FIG. 5B. Other examples of preferred embodiments include a combination of one or more of the above preferred embodiments. Still other preferred embodiments are those in which R1 is an intracellular targeting peptide sequence, such as the PENETRATIN™ sequence referenced in the examples.

Examples of still other preferred embodiments employing naturally-occuring amino acids are the isolated peptide fragments of human AF4, appearing in Table 1.

TABLE 1

| PEPTIDE | SEQ ID NO |
|---|---|
| Leu-Met-Val-Lys-Ile-Thr-Leu-Asp-Leu-Leu | AA1-10 of SEQ ID NO: 14 |
| Leu-Met-Val-Lys-Ile-Thr-Leu-Asp-Leu-Leu-Ser | AA1-11 of SEQ ID NO: 14 |
| Leu-Met-Val-Lys-Ile-Thr-Leu-Asp-Leu-Leu-Ser-Arg | AA1-12 of SEQ ID NO: 14 |
| Leu-Met-Val-Lys-Ile-Thr-Leu-Asp-Leu-Leu-Ser-Arg-Ile | AA1-13 of SEQ ID NO: 14 |
| Leu-Met-Val-Lys-Ile-Thr-Leu-Asp-Leu-Leu-Ser-Arg-Ile-Pro | SEQ ID NO: 14 |

In another example, embodiments employing naturally-occuring amino acids include the isolated peptide fragments of murine AF4, as indicated in Table 2.

TABLE 2

| PEPTIDE | SEQ ID NO |
|---|---|
| Leu-Val-Val-Lys-Ile-Thr-Leu-Asp-Pro-Leu | AA1-10 of SEQ ID NO: 15 |
| Leu-Val-Val-Lys-Ile-Thr-Leu-Asp-Pro-Leu-Thr | AA1-11 of SEQ ID NO: 15 |
| Leu-Val-Val-Lys-Ile-Thr-Leu-Asp-Pro-Leu-Thr-Arg | AA1-12 of SEQ ID NO: 15 |
| Leu-Val-Val-Lys-Ile-Thr-Leu-Asp-Pro-Leu-Thr-Arg-Ile | AA1-13 of SEQ ID NO: 15 |
| Leu-Val-Val-Lys-Ile-Thr-Leu-Asp-Pro-Leu-Thr-Arg-Ile-Pro | SEQ ID NO: 15 |

Still other examples include the isolated peptide fragments of human LAF4, indicated in Table 3.

TABLE 3

| PEPTIDE | SEQ ID NO |
|---|---|
| Leu-Trp-Val-Lys-Ile-Asp-Leu-Thr-Leu-Leu | AA1-10 of SEQ ID NO: 16 |
| Leu-Trp-Val-Lys-Ile-Asp-Leu-Thr-Leu-Leu-Ser | AA1-11 of SEQ ID NO: 16 |
| Leu-Trp-Val-Lys-Ile-Asp-Leu-Thr-Leu-Leu-Ser-Arg | AA1-12 of SEQ ID NO: 16 |
| Leu-Trp-Val-Lys-Ile-Asp-Leu-Thr-Leu-Leu-Ser-Arg-Ile | AA1-13 of SEQ ID NO: 16 |
| Leu-Trp-Val-Lys-Ile-Asp-Leu-Thr-Leu-Leu-Ser-Arg-Ile-Pro | SEQ ID NO: 16 |

Still other examples include the isolated peptide fragments of human AF5, as shown in Table 4.

TABLE 4

| PEPTIDE | SEQ ID NO |
|---|---|
| Leu-Ile-Val-Lys-Ile-Asp-Leu-Asn-Leu-Leu | AA1-10 of SEQ ID NO: 17 |
| Leu-Ile-Val-Lys-Ile-Asp-Leu-Asn-Leu-Leu-Thr | AA1-11 of SEQ ID NO: 17 |
| Leu-Ile-Val-Lys-Ile-Asp-Leu-Asn-Leu-Leu-Thr-Arg | AA1-12 of SEQ ID NO: 17 |
| Leu-Ile-Val-Lys-Ile-Asp-Leu-Asn-Leu-Leu-Thr-Arg-Ile | AA1-13 of SEQ ID NO: 17 |
| Leu-Ile-Val-Lys-Ile-Asp-Leu-Asn-Leu-Leu-Thr-Arg-Ile-Pro | SEQ ID NO: 17 |

Still another group of naturally occurring compounds of this invention include isolated peptide fragments of human or murine FMR2, as shown in Table 5.

TABLE 5

| PEPTIDE | SEQ ID NO |
|---|---|
| Leu-Trp-Val-Lys-Ile-Asp-Leu-Asp-Leu-Leu | AA1-10 of SEQ ID NO: 18 |
| Leu-Trp-Val-Lys-Ile-Asp-Leu-Asp-Leu-Leu-Ser | AA1-11 of SEQ ID NO: 18 |
| Leu-Trp-Val-Lys-Ile-Asp-Leu-Asp-Leu-Leu-Ser-Arg | AA1-12 of SEQ ID NO: 18 |
| Leu-Trp-Val-Lys-Ile-Asp-Leu-Asp-Leu-Leu-Ser-Arg-Val | AA1-13 of SEQ ID NO: 18 |
| Leu-Trp-Val-Lys-Ile-Asp-Leu-Asp-Leu-Leu-Ser-Arg-Val-Pro | SEQ ID NO: 18 |

The following Table 6 indicates a variety of compounds of the present invention, listed in single letter amino acid code, for convenience.

TABLE 6

| SEQUENCE | SEQ ID NO: | SEQUENCE | SEQ ID NO: |
|---|---|---|---|
| LMVKITLDLLSRIP | 19 | LWVKIDLDLLSRV | 27 |
| LMVKITLDLL | 36 | LMVRITLDML | 28 |
| LMVRITLDLL | 20 | LMVHITLDML | 29 |
| LMIKITLDLLS | 21 | LFVKITLDLM | 30 |
| LFVKITLDLL | 22 | LFVHITLDLM | 31 |
| LFVHITLDLL | 23 | LFVRITLDLM | 32 |
| LFVRITLDLL | 24 | LIVEITLDLLS | 33 |
| LIVKITLDLLS | 25 | LIVRITLDFL | 34 |
| LIVRITLDLL | 26 | LIVHITLDFL | 35 |
| LIVHITLDLL | 37 | LIVKVTLDLLS | 67 |
| LLVKITVDLLS | 38 | LLVHITLDLF | 68 |
| LLVHITLDLL | 39 | LLVRITLDLF | 69 |
| LLVRITLDLL | 40 | LWVKITLDIL | 70 |
| LWVKITLDLL | 41 | LWVHITLDIL | 71 |
| LWVHITLDLL | 42 | LWVRITLDIL | 72 |
| LWVRITLDLL | 43 | LYVKITLDLI | 73 |

TABLE 6-continued

| SEQUENCE | SEQ ID NO: | SEQUENCE | SEQ ID NO: |
| --- | --- | --- | --- |
| LYVKITLDLL | 44 | LYVHITLDLI | 74 |
| LYVHITLDLL | 45 | LYVRITLDLI | 75 |
| LYVRITLDLL | 46 | LVVKITLDWL | 76 |
| LVVKITLDLL | 47 | LVVHITLDWL | 77 |
| LVVHITLDLL | 48 | LVVRITLDWL | 78 |
| LVVRITLDLL | 49 | LVVKITLDLW | 79 |
| LVVKITLDYL | 50 | LVVHITLDLW | 80 |
| LVVHITLDYL | 51 | LVVRITLDLW | 81 |
| LVVRITLDYL | 52 | LVVKITLDVL | 82 |
| LVVKITLDLY | 53 | LVVHITLDVL | 83 |
| LVVHITLDLY | 54 | LVVRITLDVL | 84 |
| LVVRITLDLY | 55 | LVVKITLDLV | 85 |
| LVVHIRLDLY | 56 | LVVHITLDLV | 86 |
| Acetyl-LMVKITLDLL | 57 | LMVRITLDML | 87 |
| Acetyl-VLMVRITLDLL | 58 | LMVHITLDML | 88 |
| LVVKITLDPLTRIP | 59 | LFVKITLDLM | 89 |
| LWVKIDLTLLSRIP | 60 | LFVHITLDLM-(Dap) | 90 |
| LIVKIDLNLLTRIP | 61 | LFVRITLDLM | 91 |
| LWVKIDLDLLSRVP | 62 | LVVKITLDPL | 92 |
| LWVKIDLDLLSRVP | 63 | Acetyl-LWVKIDLTLL | 93 |
| LIVRITLDL-(N-Me)L | 64 | LWVKIDLDLL | 94 |
| LMVKITLDLL { } LLDLTIKVML | 65 | LVVKIT-(N-Me)LDLV | 95 |
| LMVKIDLDLLSRIP | 66 | LWVKIDLDLLSRIP | 96 |
| LMVKITLDLLSRIP | 97 | LWVKITLDLLSRIP | 100 |
| KKKKKKRKVLIVRIDLDLS | 98 | KKKRKVLIVRIDLDLS | 101 |
| LIVKIALALL | 99 | C LIVKIALALL | 102 |

In another embodiment, multiple compounds of the formula described above may be organized in multimeric constructs or compositions. For example, optional amino acids (e.g., -Gly-Ser-) or other amino acid or chemical compound spacers may be included at the N- or C-termini of the peptides for the purpose of linking two or more peptides together or to a carrier. This composition may take the form of one or more of the above-described compounds expressed as a synthetic peptide coupled to a carrier protein. Alternatively, a composition may contain multiple peptides, each expressed as a multiple antigenic peptide, optionally coupled to a carrier protein. Alternatively, the selected peptides may be linked sequentially and expressed as a recombinantly produced protein or polypeptide. In one embodiment, multiple peptides are linked sequentially, with and without spacer amino acids therebetween, to form a larger recombinant protein. Alternatively, the recombinant protein may be fused in frame with a carrier protein or transporter protein, such as described in the examples.

In one embodiment of a multimeric construct containing at least two of the above-defined compounds of the formula of the present invention (which may be the same or different peptides of the formula), one peptide is attached to any amino acid of the other peptide(s). Any number of additional peptides may be attached to any amino acid of the other peptides in the composition. In another embodiment of a multimeric composition containing at least two peptides, the second or additional peptides are attached to a branched construct of the other peptides in the composition. Alternatively, each additional peptide is covalently linked to R2 of another peptide in the composition.

In another embodiment of a multimeric construct or composition containing at least two of the peptides, at least one or more of the peptides is attached to a carrier, preferably an immunologically inert carrier. In another embodiment, one or more of said peptides is a synthetic peptide fused to a carrier protein. Still alternatively multiple of the above-described peptides with or without flanking sequences, may be combined sequentially in a polypeptide. The peptides or this polypeptide may be coupled to the same carrier, or different peptides may be coupled individually as peptides to the same or a different carrier protein.

Suitable carrier proteins may enhance stability or delivery, improve the production, or change the activity spectrum of the peptide. As a few well-known examples, such carrier moieties may be human albumin, polyethylene glycol, other biopolymers or other naturally or non-naturally occurring polymers. In one embodiment, the moiety is desirably a protein or other molecule which can enhance the stability of the peptide or enhance its penetration into the targeted cell. One of skill in the art can readily select an appropriate conjugation moiety.

In yet another embodiment, the peptides may be in the form of a multiple antigenic peptide ("MAP"). Such a construct may be designed employing the MAP system described by Tam, Proc. Natl. Acad. Sci. USA, 1988 85:5409–5413. This system makes use of a core matrix of lysine residues onto which multiple copies of the same peptide of the invention are synthesized as described [see, e.g., D. Posnett et al., J. Biol. Chem., 1988 263(4):1719–1725]. Each MAP contains multiple copies of one or more of the peptides or this invention. One embodiment of a MAP contains at least three, and preferably four or more peptides. One preferred embodiment contains a β-alanine substituent on the poly-lysine core.

One of skill in the art may readily make any number of multimeric constructs from the peptides of the formula of the present invention with resort to only conventional skills and knowledge in light of this specification. All such multimeric compositions and constructs are intended to be included in this invention.

B. Methods of Production

Such peptides and multimeric compositions may be produced synthetically or recombinantly by conventional methods. Specific embodiments of pyrrhocoricin-derived anti-bacterial/anti-fungal peptides of this invention are disclosed in detail in Example 1 below. Preferably, the peptides of the invention are prepared conventionally by known chemical synthesis techniques. Among such preferred techniques known to one of skill in the art are included the synthetic methods described by Merrifield, J. Amer. Chem. Soc., 1963 85:2149–2154 or as detailed in Example 1.

Alternatively, the peptides or multimeric compositions of this invention may be prepared by known recombinant DNA techniques by cloning and expressing within a host microorganism or cell a DNA fragment carrying a nucleic acid sequence encoding one of the above-described peptides.

The modified compounds specifically identified herein and others within the teachings of this specification can all be readily tested for the required biological function, e.g., the ability to disrupt the binding between the AF4 and AF9 proteins in mammalian cells in vitro and in vivo. The resulting peptide or multimeric construct is screened for biological activity and/or metabolic stability by in vitro and in vivo assays, such as those described in the examples and in the art. These peptides generally have "significant" metabolic stability in mammalian serum, i.e., the peptides are stable for at least 2 hours in serum. More preferred peptides are stable for at least 4 hours in serum. Still more preferred peptides of this invention are stable in serum for greater than 8 hours.

C. Pharmaceutical Compositions of the Invention and Methods of Treatment

The compositions of this invention are designed to treat or prevent the development or progression of certain leukemias in mammalian subjects, e.g., humans. At least one, or alternatively, several of the peptides or multimeric constructs of the present invention may be formulated into a pharmaceutical composition with a pharmaceutically acceptable carrier and other optional components. For use in such compositions, the selected peptide may be produced preferably synthetically, but also recombinantly, as disclosed above.

The compounds may be employed in pharmaceutical compositions individually or in combination. Alternatively, for the purposes of enhancing pharmacokinetics or bioavailability without eliciting immune responses, one or more peptides may be fused or conjugated to other moieties as described above. Any number of single peptides or multimeric constructs may be mixed together to form a single composition.

Similarly the compounds may be coupled to penetration enhancer or transporter compounds to enhance transport of the compound into the cell.

Proper transport and localization is demonstrated by a variety of detection methods such as, for example, fluorescence microscopy, confocal microscopy, electron microscopy, autoradiography, or immunohistochemistry.

It should also be added that other methods that have also been employed for delivery of proteins, may be useful in this invention. Such methods of protein delivery into a cell include scrape loading, calcium phosphate precipitates, liposomes, electroporation, membrane fusion with liposomes, high velocity bombardment with peptide-coated microprojectiles, incubation with calcium-phosphate-peptide precipitate, DEAE-dextran mediated transfection, and direct micro-injection into single cells. Chemical addition of a lipopeptide (P. Hoffmann et al., Immunobiol., 1988 177, pp. 158–70) or a basic polymer such as polylysine or polyarginine (W. -C. Chen et al., Proc. Natl. Acad. Sci. USA, 1978 75, pp. 1872–76). Folic acid has been used as a transport moiety (C. P. Leamon and Low, Proc. Natl. Acad. Sci USA, 1991 88, pp. 5572–76). *Pseudomonas* exotoxin has also been used as a transport moiety (T. I. Prior et al., Cell, 1991 64, pp. 1017–23).

Such methods may be substituted for the peptide/protein transport moiety, if desirable.

As pharmaceutical compositions, the compounds can be utilised by themselves or as functionally effective derivatives. These compounds are admixed with a pharmaceutically acceptable vehicle or carrier suitable for administration as a protein composition. These peptides may be combined in a single pharmaceutical preparation for administration. Suitable pharmaceutically acceptable carriers for use in a pharmaceutical proteinaceous composition of the invention are well known to those of skill in the art. Such carriers include, for example, water, saline, buffered saline, alcohols, gum Arabic, vegetable oils, benzyl alcohols, polyethylene glycols, gelatin, carbohydrates, such as lactose, amylase or starch, magnesium stearate, talc, silicic acid, viscous paraffin, perfume oil, fatty acid monoglycerides and diglycerides, pentaerythritol fatty acid esters, hydroxymethylcellulose, polyvinylpyrrolidone, liposomes, oil in water emulsions and others. The compositions may further include a detergent to make the peptide more bioavailable, e.g., octylglucoside. The present invention is not limited by the selection of the carrier or detergent.

The compounds are also useful in the form of a salt with an acid. The compounds have at least one amino/amine groups which can form salts in accordance with the invention. Where two or more amino groups are present in the compound, a formulation of mixed salts can be prepared. Acids which can be used preferably include compatible inorganic acids such as hydrochloric and organic acids (or salts thereof) more preferably those occurring in living organisms, including but not limited to oxalic acid, glucuronic acid, pyruvic acid, lactic acid, citric acid, isocitric acid -ketoglutaric acid, succinic acid, malic acid, and oxaloacetic acid. In the preferred case of an aqueous solution, the desired anion can be added either as the free acid, or a salt, preferably one which is highly soluble in water, for example the sodium or potassium salts, but also the lithium, magnesium, calcium or ammonium salts. Moreover, these salts can be used either in anhydrous or hydrated forms. For example citric acid can be used as the anhydrous free acid, the monohydrate free acid, the anhydrous trisodium salt, or the dihydrate trisodium salt. These salts can be prepared by the methods described in WO 96/02269.

Alternatively, the pharmaceutical compositions contain sequences which express the peptide or proteins of the invention in the host cell, which peptides are then secreted from the host cells. Suitable vehicles for direct DNA, plasmid nucleic acid, or recombinant vector administration include, without limitation, saline, sucrose, protamine, polybrene, polylysine, polycations, proteins, or spermidine, etc. [See e.g., International Patent Application No. WO94/01139].

The pharmaceutical compositions may also be formulated to suit a selected route of administration, and may contain ingredients specific to the route of administration [see, e.g., Remington: The Science and Practice of Pharmacy, Vol. 2, 19$^{th}$ edition (1995)]. A non-exclusive list of auxiliary agents are lubricants, preservatives, stabilizers, wetting agents, emulsifiers, salts for influencing osmotic pressure, buffers, coloring, flavoring nad/or aromatic substances and dthe like that do not deleteriously react with the active compounds. The preparation of these pharmaceutically acceptable compositions, from the above-described components, having appropriate pH isotonicity, stability and other conventional characteristics is within the skill of the art.

A method of treating or preventing the development of a leukemia involves administering to a mammalian subject, preferably a human, an effective amount of a pharmaceutical composition described above. The method is useful in the treatment of acute leukemias, such as those specifically identified herein. The method may also be useful to treat or prevent other types of leukemia or cancer in which the binding of the AF4 and AF9 proteins play a role. The leukemia to be treated may include, but is not limited to a leukemia characterized by a t(4:11)(p21:q23) chromosomal translocation or a leukemia characterized by a t(9:11)(p22:q23) chromosomal translocation. Other leukemias treatable by the methods and compounds of this invention can include those with chromosomal abnormalities in 19p13, 9p22, 2q11, and 5q31. Still other leukemias which can be treated, preferably prophylactically, by the compounds of this invention include chemotherapy-induced secondary leukemias, such as occur as a consequence of breast cancer chemotherapy, for example.

According to this invention, a pharmaceutical composition as described above may be administered by any appropriate route, but preferably by a route which transmits the peptide directly into the blood, e.g., intravenous injection. Subcutaneous injection is also a useful mode of administration. Other routes of administration include, without limitation, oral, intradermal, transdermal, intraperitoneal, intramuscular, intrathecal, mucosal (e.g., intranasal), and by inhalation.

The amount of the protein, peptide or nucleic acid sequences of the invention present in each effective dose is selected with regard to consideration to the half-life of the compound, the identity and/or stage of the leukemia, the patient's age, weight, sex, general physical condition and the like. The amount of active component required to induce an effective apoptotic effect on leukemia cells without significant adverse side effects varies depending upon the pharmaceutical composition employed and the optional presence of other components. Generally, for the compositions containing protein/peptide, or fusion protein, each dose will comprise between about 5 µg peptide/kg patient body weight to about 10 mg/kg. Generally, a useful therapeutic dosage is between 1 to 5 mg peptide/kg body weight. Another embodiment of a useful dosage may be about 500 µg/kg of peptide. Other dosage ranges may also be contemplated by one of skill in the art. For example, dosages of the peptides of this invention may be similar to the dosages discussed for other peptide cancer therapeutics.

Initial doses of a composition of this invention may be optionally followed by repeated administration for a duration selected by the attending physician. Dosage frequency may also depend upon the factors identified above, and may range from 1 to 6 doses per day for a duration of about 3 days to a maximum of no more than about 1 week. The compositions of this invention may also be administered as a continuous infusion for about 3–5 days, the specific dosage of the infusion depending upon the half-life of the compound. The compounds of this invention may also be incorporated into chemotherapy protocols, involving repetitive cycles of dosing. Selection of the appropriate dosing method would be made by the attending physician.

D. Use of the Peptides of This Invention in Drug Design, Screening and Development The peptides and polynucleotide sequences of the present invention may also be used in the screening and development of chemical compounds, small molecules or proteins which mimic the structure or activity of the peptides of this invention, and thus have utility as therapeutic drugs for the treatment of leukemias and other cancers involving the interplay of AF4 and AF9. These peptides may also be employed in assays to identify and isolate the stereospecific receptor located in the leukemia cells against which the peptides are effective and with which they interact to achieve their apoptotic effect. Identification of this receptor may also permit use of a variety of known techniques to design and develop other drugs having the apoptotic effect of the peptides of this invention.

In one such embodiment, the peptides are employed in a suitable competitive assay method with test compounds to assess the ability of the test compound to competitively displace the peptide from binding to AF4 and AF9. The steps of such a competitive assay may be readily determined by one of skill in the art. Where desired, and depending on the assay selected, a leukemic cell to which the selected peptide(s) are known to bind may be immobilized directly or indirectly on a suitable surface, e.g., in an ELISA format. Such immobilization surfaces are well known. For example, a wettable inert bead may be used. Further, the ligand may be bound to a 96 well plate. Thereafter selected amounts of the test compounds and the peptides of this invention are exposed to the immobilized cell and those test compounds selected which can compete with the peptides for binding to the AF4/AF9 proteins in the immobilized cell. Once those test compounds which compete with the peptides for binding are identified, they may be further screened for biological activities in the methods described in the examples below. It is within the skill of the art to prepare other conventional assay formats for identification of test compounds which compete with the peptides of this invention for binding to the AF9 protein.

As another example, a comparative assay may be performed using an animal model or in vitro assay such as those described in the Examples below, or employing a leukemia cell line known to rely on AF4/AF9 binding for its proliferation. A test compound may be added to the cell line and the effect of the test compound compared with the effect of a compound defined by the formula herein.

The compounds of this invention can be used to identify other molecules or analogs that bind to the same sequence on the AF9 protein. For example, preferably the peptides carry a fluorescing or fluoresceinating reporter group, such as a fluorescein-Lys moiety. A 2 nM solution of fluorescein-labeled test peptide is mixed with a PBS solution of the cell in which the concentration of the AF9 receptor varies from 1 nM to 100 µM. The binding curve is measured by fluorescence polarimetry.

Identification of useful test compounds permit the screening and development of identification, e.g., the screening of combinatorial libraries, of non-peptide libraries which mimic the activity of a peptide compounds of this invention. For example, one of the peptides described herein, e.g., PFWT, may be employed to screen a small non-peptide molecule library for compounds that disrupt AF4-AF9 complexes using a high throughput in vitro assay. The candidate molecules are then tested in leukemia cell lines and normal hematopoietic cells, such as described below in the Examples. The candidate small molecule may be further tested in NOD (non-obese diabetic) SCID (severe combined immunodeficiency) mouse models of t(4:11) human leukemia or a t(4:11) leukemia human xenograft. Other animal models of leukemia can also be employed.

Other assays and techniques also exist for the identification and development of compounds and drugs which mimic the structure or activity of a peptide of this invention. These include the use of phage display system for expressing the peptide(s), and the use of a culture of transfected *E. coli* or other microorganisms to produce the peptides for binding studies of potential binding compounds. See, for example, the techniques. described in G. Cesarini, FEBS Letters, 1992 307(1):66–70; H. Gram et al, J. Immunol. Meth., 1993

161:169–176; C. Summer et al, Proc. Natl. Acad. Sci., USA, 1992 89:3756–3760, incorporated by reference herein.

Other conventional drug screening techniques may be employed using the peptides of this invention. As one example, a method for identifying compounds which specifically bind to a peptide of this invention can include simply the steps of contacting a selected peptide with a test compound to permit binding of the test compound to the peptide; and determining the amount of test compound, if any, which is bound to the peptide. Such a method may involve the incubation of the test compound and the peptide immobilized on a solid support.

Typically, the surface containing the immobilized ligand is permitted to come into contact with a solution containing the peptide and binding is measured using an appropriate detection system. Suitable detection systems include the streptavidin horseradish peroxidase conjugate, direct conjugation by a tag, e.g., fluorescein. Other systems are well known to those of skill in the art. This invention is not limited by the detection system used.

Another method of identifying compounds which specifically bind to the peptides of this invention can include the steps of contacting the peptide, immobilized on a solid support with both a test compound and a proposed receptor for the peptide to permit binding of the receptor to the peptide; and determining the amount of the receptor which is bound to the peptide.

A compound which has structural similarity to the peptide, or the binding portion of the peptide to the AF9 receptor may also be computationally evaluated and designed by means of a series of steps in which chemical entities or fragments are screened and selected for their ability to associate with the peptides of this invention. One skilled in the art may use one of several methods to screen chemical entities or fragments for their ability to mimic the structure of these peptides and more particularly to identify the peptide structure that binds with the stereospecific receptor of the compounds specifically described herein. This process may begin by visual inspection of, for example, a three dimensional structure of the peptides of this invention on the computer screen. Selected fragments or chemical entities may then be positioned in a variety of orientations to determining structural similarities, or docked, within a putative binding site of the peptide.

Specialized computer programs that may also assist in the process of selecting fragments or chemical entities similar to the peptides, or entities which can interact with the peptides and thus mimic the receptor, include the GRID program available from Oxford University, Oxford, UK. (P. J. Goodford, J. Med. Chem., 1985 28:849–857); the MCSS program available from Molecular Simulations, Burlington, Mass. (A. Miranker and M. Karplus, Proteins: Structure, Function and Genetics, 1991 11:29–34); the AUTODOCK program available from Scripps Research Institute, La Jolla, Calif. (D. S. Goodsell and A. J. Olsen, Proteins: Structure, Function, and Genetics, 1990 8:195–202); and the DOCK program available from University of California, San Francisco, Calif. (I. D. Kuntz et al, J. Mol. Biol., 1982 161:269–288), and software such as Quanta and Sybyl, followed by energy minimization and molecular dynamics with standard molecular mechanics force fields, such as CHARMM and AMBER. Additional commercially available computer databases for small molecular compounds include Cambridge Structural Database, Fine Chemical Database, and CONCORD database (for a review see Rusinko, A., Chem. Des. Auto. News, 1993 8:4447 (1993).

Once suitable chemical entities or fragments have been selected, they can be assembled into a single compound, agonist or antagonist. Assembly may proceed by visual inspection of the relationship of the fragments to each other on the three-dimensional image displayed on a computer screen in relation to the structure of the peptide. Useful programs to aid one of skill in the art in connecting the individual chemical entities or fragments include the CAVEAT program [P. A. Bartlett et al, "CAVEAT: A Program to Facilitate the Structure-Derived Design of Biologically Active Molecules", in *Molecular Recognition in Chemical and Biological Problems*", Special Pub., Royal Chem. Soc. 78, pp. 182–196 (1989)], which is available from the University of California, Berkeley, Calif.; 3D Database systems such as MACCS-3D database (MDL Information Systems, San Leandro, Calif.) (see, e.g., Y. C. Martin, J. Med. Chem., 1992 35:2145–2154); and the HOOK program, available from Molecular Simulations, Burlington, Mass.

Compounds that mimic a peptide of this invention may be designed as a whole or "de novo" using methods such as the LUDI program (H. -J. Bohm, J. Comp. Aid. Molec. Design, 1992 6:61–78), available from Biosym Technologies, San Diego, Calif.; the LEGEND program (Y. Nishibata and A. Itai, Tetrahedron, 1991 47:8985), available from Molecular Simulations, Burlington, Mass.; and the LeapFrog program, available from Tripos Associates, St. Louis, Mo. Other molecular modeling techniques may also be employed in accordance with this invention. See, e.g., N. C. Cohen et al, J. Med. Chem., 1990 33:883–894. See also, M. A. Navia and M. A. Murcko, Current Opinions in Structural Biology, 1992 2:202–210. For example, where the structures of test compounds are known, a model of the test compound may be superimposed over the model of the peptide of the invention. Numerous methods and techniques are known in the art for performing this step, any of which may be used. See, e.g., P. S. Farmer, Drug Design, Ariens, E. J., ed., Vol. 10, pp 119–143 (Academic Press, New York, 1980); U.S. Pat. No. 5,331,573; U.S. Pat. No. 5,500,807; C. Verlinde, Structure, 1994 2:577–587; and I. D. Kuntz, Science, 1992 257: 1078–1082. The model building techniques and computer evaluation systems described herein are not a limitation on the present invention.

Thus, using these computer evaluation systems, a large number of compounds may be quickly and easily examined and expensive and lengthy biochemical testing avoided. Moreover, the need for actual synthesis of many compounds is effectively eliminated.

Similarly the nuclear magnetic resonance structure of the C-terminus of AF9 in solution with a peptide of this invention may be determined and then refined with point mutational analyses. This "receptor" structure is then itself useful in the design of new compounds with bioactivity.

Once identified by the modeling techniques, the proposed new compound may be tested for bioactivity using standard techniques, such as the in vitro assay of the examples. Suitable assays for use herein include, but are not limited to, the assays shown below in the examples to detect the AF9/AF4 disruptive and apoptotic effect of the peptides of this invention. However, other assay formats may be used and the assay formats are not a limitation on the present invention.

EXAMPLES

The following examples illustrate various aspects of this invention. These examples do not limit the scope of this invention which is defined by the appended claims.

Example 1

Mapping the AF9 Binding Domain of AF4

Leukemic blasts of nearly 50% of infants with ALL express chimeric MLL-AF4 fusion proteins (Felix et al, 2000, cited above). The MLL fusion partner AF4 is a protein that interacts with AF9, another commonly encountered MLL fusion protein (Erfurth, F., et al, 2004, cited above). Using yeast two-hybrid assays the minimal interaction domains of the two proteins were determined.

AF4 binds the carboxy-terminus (C-terminus) of AF9, a region that is predicted to contain two 60 helices (Slany, R. K., et al, 1998, cited above). The complete amino-proximal helix (helix 1) is required for binding but partial truncation of the second α helix of AF9 still supports protein interaction with AF4 in yeast two-hybrid assays (Srinivasan, R. S., et al., Oncogene 2003 22: 3395–3406). An exceptionally small region of human AF4 encompassing amino acid positions 760–770 SEQ ID NO: 103 of the 1200 amino acid AF4 sequence is found to be sufficient for its interaction with the C-terminus of AF9. This small domain of AF4 is highly conserved in the AF4 homologs AF5, LAF4 and FMR2 (FIG. 1).

Furthermore, this portion of the molecule is retained in leukemia cells expressing MLL-AF4, MLL-AF5 and MLL-LAF4 (Domer, P. H., et al., Proc Natl Acad Sci USA 1993 90: 7884–7888; Taki, T. et al, Proc Natl Acad Sci USA 1999 96: 14535–40; von Bergh, A. R., et al, Genes Chromosomes Cancer 2002 35: 92–6). Web-based algorithms to discern structural features of polypeptide sequences predict that the binding domain lacks ordered secondary structure.

To determine the contribution of individual amino acids to protein binding and identify amino acid positions in the compound formula that are susceptible to modification and yet permit protein binding, mutational analysis of ten residues within the AF9 interaction domain of AF4 was performed. Individual amino acid substitutions were individually introduced into the isolated 11 amino acid fragment Leu-Met-Val-Lys-Ile-Thr-Leu-Asp-Leu-Leu-Ser SEQ ID NO: 104 of the approximately 1200 amino acid sequence of the human AF4 protein as follows. For the first set of mutations, each amino acid at positions 2 through 10 was individually mutated to an Ala, a hydrophilic residue. Another mutant was created by deleting the carboxy terminal Ser. In another mutant, the Val at position 3 was replaced with Ile. In two other mutants, the Lys at position 4 was replaced with Arg or Glu. In three other mutants the Ile at position 5 or the Leu at position 7 or the Leu at position 10 were individually replaced with Val.

These mutant or substituted AF4 peptide proteins were then tested in yeast two-hybrid assays to assess binding to the carboxy-terminus of AF9. Briefly described, yeast two-hybrid plasmid vectors encoding the Gal4 DNA binding domain fused to amino acids 760–770 of human AF4 were produced by annealing complementary single strand oligonucleotides followed by direct cloning into pGBT9. The AF4 sequence of each plasmid was verified. Yeast strain PJ69–4A was used to test two-hybrid protein interactions by measuring adenine prototrophy as described in Srinivasan, R. S., et al., 2003, cited above.

The individual replacement of the naturally occurring amino acids with the hydrophilic residue Ala showed that bulky hydrophobic side chains are important at residues Met2, Val 3, Ile5, Leu7 and Leu10, because the mutant protein containing the Ala substitution at those amino acid positions failed to interact with AF9 in the assay. In contrast, Ala substitution of the polar residues Thr6 and Asp8 (except Lys4) did not interfere with protein binding. The Ala substitution did extinguish binding activity for Lys4. The positive charge associated with Lys4 plays an important role as substitution of Arg4 for Lys4 still supported binding, while Glu4 blocked the two-hybrid interaction and extinguished binding activity. The substitution of the hydrophobic residue Ile3 for the naturally-occurring hydrophobic residue Val3 also extinguished activity. Similarly, the substitution of Val5 for Ile5 or Val7 for the hydrophobic Leu7 also extinguished activity, but the substitution of Val10 for Leu10 showed that the mutant protein interacted as well as wild-type protein. The substitution of the hydrophilic Ala9 for the hydrophobic Lue9 demonstrated a weak, but positive, two-hybrid interaction. Finally, the mutant that eliminated the Ser at position 11 had no effect on the binding activity of the mutant peptide.

Example 2

Development of a Bioactive Peptide

To assess whether a synthetic peptide that mimics the AF9 binding site of AF4 will compete with AF4 for AF9 binding and interfere with protein dimerization, a 14 residue peptide corresponding to amino acids 759–771 of mouse FMR2 (designated PFWT below) was synthesized by United Biochemicals (Seattle, Wash.) and purified to >85% by high pressure liquid chromatography. Non-conjugated peptides used exclusively for in vitro assays were synthesized by the Peptide Research Laboratory at Tulane University. The mouse and human FMR2 sequences are identical at these positions and the amino acid residues are highly conserved among all AF4 family members (FIG. 1).

Peptide PFWT has the sequence Leu-Trp-Val-Lys-Ile-Asp-Leu-Asp-Leu-Leu-Ser-Arg-Val-Pro or LWVKIDLD-LLSRVP (SEQ ID NO: 2) and is coupled or conjugated at its amino terminal leucine to the PENETRATIN™ penetration enhancer or transporter sequence, which has the sequence Arg-Gln-Ile-Lys-Trp-Phe-Gln-Asn-Arg-Arg-Met-Lys-Trp-Lys-Lys or RQIKWFQNRRMKWKK (SEQ ID NO: 105). The penetration enhancer facilitates translocation of the peptide across the cell membrane (Derossi, D., et al., J Biol Chem 1994 269: 10444–10450).

As a control, a similar peptide was designed with Glu in position 3 and Ser in position 5, and called PFmut. PFmut has the sequence Leu-Trp-Glu-Lys-Ser-Asp-Leu-Asp-Leu-Leu-Ser-Arg-Val-Pro or LWEKSDLDLLSRVP (SEQ ID NO: 106) and is similarly conjugated to the enhancer as described above. Pfmut's mutations attentaute FMR2's interaction with AF9.

PFWT and PFmut are soluble in phosphate buffered saline (PBS) at a concentration of 1 mg/ml and in dimethylsulfoxide (DMSO) at >50 mg/ml (data not shown). In the initial experiments, peptides were dissolved in PBS but were dissolved in DMSO for the majority of the subsequent experiments.

Example 3

The Peptide PFWT Disrupts AF4-AF9 Complexes In Vitro

A. GST Pull-Down Assay

To determine if the synthetic peptide could disrupt the AF4-AF9 interaction in vitro, and to determine if the peptide disrupted other binding events with AF9, the following assay was performed. In additional to AF4, the carboxy-terminus of AF9 binds at least two other proteins, the Polycomb protein MPc3 and mBCoR, the mouse homolog of the human BCL-6 corepressor protein (Srinivasan 2003 and Hemenway 2001, both cited above). Using a yeast three hybrid assay similar to that described in Example 1, it was previously shown that mBCoR and FMR2 (an AF4 homolog) can simultaneously bind AF9. On the other hand, MPc3-AF9 dimeric protein complexes do not appear to form stable ternary complexes with either mBCoR or FMR2 (Srinivasan et al, 2003 cited above). The sequences of human AF4 and AF9 and murine MPc3 and BCoR can be found in the NCBI database under Accession Nos. P51825, P42568, Q9QXV1, and AAN85318, respectively, incorporated by reference herein.

Recombinant proteins consisting of glutathione-S-transferase (GST) fused to either (a) amino acids 749–775 of human AF4 SEQ ID NO: 107, (b) amino acids 202–362 of MPc3 SEQ ID NO: 108 or (c) amino acids 925–1759 of mBCoR SEQ ID NO: 109 were isolated from *E. coli*. These fusion proteins were immobilized on 50 µl glutathione agarose matrix. (i.e., glutathione Sepharose™ beads). Biotinylated AF9 was synthesized by coupled in vitro transcription and translation (Promega) of a Hind III restriction fragment of human AF9 cDNA. This fragment encodes the C-terminal 368 aa of AF9 SEQ ID NO: 114.

Binding of biotinylated AF9 was performed as previously described (Srinivasan, R. S., et al., 2003, cited above; Hemenway, C. S., et al., Oncogene 2001 20: 3798–3805). Briefly, 25 µl of crude AF4 protein extract was immobilized on glutathione coated 96 well plates (Sigma) followed by extensive washing with TBS containing 0.05% Tween (TBST). Biotinylated AF9 was diluted 1:30 in TBST buffer and 30 µl of the AF9 mixture was applied to the wells containing immobilized GST-AF4 and incubated overnight at 4° C. in the presence or absence of varying concentrations (10 µg/ml, 25 µg/ml or 100 µ/ml) of peptide PFWT, peptide PFmut, or the control vehicle DMSO.

After extensive washing with TBST, proteins were resolved by SDS-PAGE and transferred to nitrocellulose. 50 µl 1:1000 dilution of AP-conjugated streptavidin was added to the wells and incubated at 4° C. for 2 h. After additional washing, 150 µl of p-nitrophenyl phosphate (pNPP) in pre-mixed stabilized solution (Sigma) was added to each of the wells and incubated in the dark at room temperature for 2 h. Biotinylated AF9 was revealed by colorimetric detection on western blot using alkaline phosphatase conjugated streptavidin. Alkaline phosphatase activity was measured by determining the optical density of the samples at 405 nm with a plate spectrophotometer. All assays were done in replicates of four.

The resulting gels (not shown) demonstrated that AF9 is displaced from the GST-AF4(749–775) affinity matrix by PFWT, but that binding was still apparent in the presence of PFmut at 100 µg/ml. AF9 appeared as a doublet in this assay. The blot revealed that immobilized GST-AF4 retains AF9 in vitro but, at a concentration of 10 µg/ml, PFWT peptide completely blocks AF4-AF9 binding. In contrast, PFmut does not interfere with AF4-AF9 binding under these experimental conditions.

However, the AF9 binding proteins MPc3 and mBCoR are not displaced by 25 µg/ml PFWT. PFWT had no effect on the binding of AF9 to the Polycomb protein, MPc3 or the BCL-6 corepressor, BCoR.

Hence, PFWT specifically disrupts the AF4-AF9 interaction in vitro, but does not interfere with the binding of MPc3 or mBCoR to AF9.

B. Enzyme-Linked Protein Binding Assay

Figure 2A:
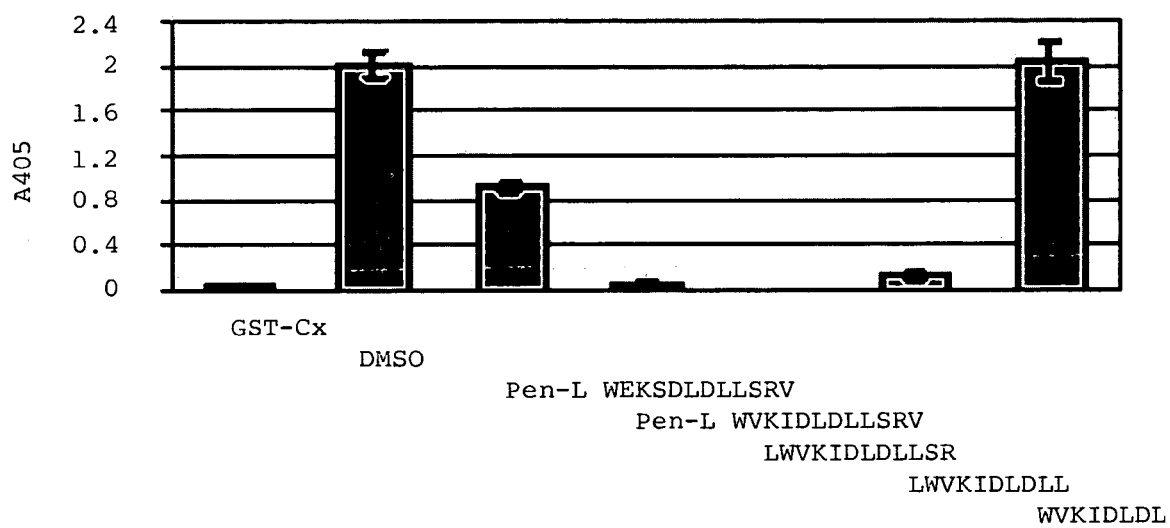
FIG. 2A provides the results of the GST pull down assay described in detail in Example 3 and demonstrates that a compound of the present invention disrupts the interaction of AF4 and AF9 in vitro. A fusion protein of the transporter protein PENETRATIN™ (Pen) bound to the amino terminal of Leu-Trp-Val-Lys-Ile-Asp-Leu-Asp-Leu-Leu-Ser-Arg-Val-Pro (SEQ ID NO: 2, referred to as PFWT or to amino acids 1–14 of SEQ ID NO: 2) is shown in column 4 to almost completely block AF9 binding. Another compound formed by a fusion protein of Pen to Leu-Trp-Glu-Lys-Ser-Asp-Leu-Asp-Leu-Leu-Ser-Arg-Val-Pro (SEQ ID NO: 3, referred to as Pfmut PFWT or to amino acids 1–14 of SEQ ID NO: 3) in column 3 also interferes with AF9 binding, but a significant amount of AF9 remains bound in the well. Peptides (formed of SEQ ID NO: 111 in column 5 and SEQ ID NO: 112 in column 6) lacking the Pen transduction sequence also block AF9 binding. Note, however, the effect of the peptide SEQ ID NO: 113 in column 7.
Figure 2B:
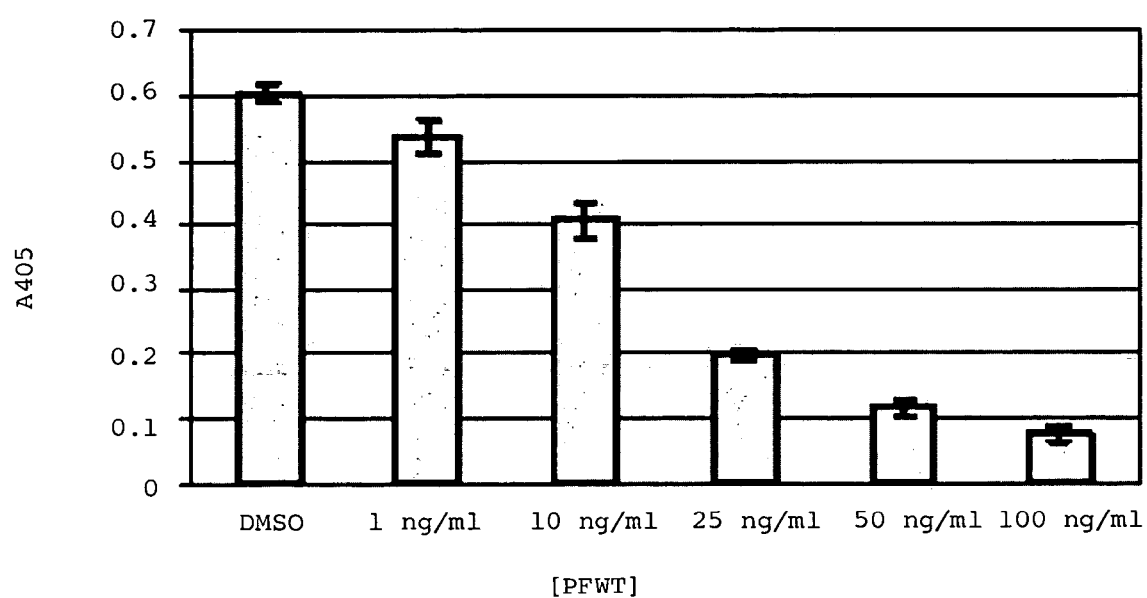
FIG. 2B demonstrates that PFWT displaces AF9 from AF4 in a concentration-dependant fashion. Protein binding assays were performed as in Example 3 and FIG. 2A described above.

Next, an enzyme-linked protein binding assay was developed as a potential high throughput tool to semi-quantitatively assess the ability of various compounds to disrupt the AF4-AF9 interaction in vitro (FIGS. 2A and 2B).

GST-AF4 (749–775) SEQ ID NO: 107 was bound to glutathione-coated 96-well plates and incubated with biotinylated AF9 in conjunction with 20 µg/ml of the following peptides:

(a) Pen-LWEKSDLDLLSRV, a fusion protein of PENETRATIN™ transporter peptide to the amino terminus of Leu-Trp-Glu-Lys-Ser-Asp-Leu-Asp-Leu-Leu-Ser-Arg-Val (SEQ ID NO: 110, PFmut), (b) Pen-LWVKIDLDLLSRV, a fusion protein of the transporter protein PENETRATIN™ to the amino terminus of Leu-Trp-Val-Lys-Ile-Asp-Leu-Asp-Leu-Leu-Ser-Arg-Val (SEQ ID NO: 2; or PFWT), (c) LWVKIDLDLLSR or Leu-Trp-Val-Lys-Ile-Asp-Leu-Asp-Leu-Leu-Ser-Arg (SEQ ID NO: 111);

(d) LWVKIDLDLL or Leu-Trp-Val-Lys-Ile-Asp-Leu-Asp-Leu-Leu- (SEQ ID NO: 112);

(e) WVKIDLDL or Trp-Val-Lys-Ile-Asp-Leu-Asp-Leu (SEQ ID NO: 113), or with (f) DMSO, or (g) GST-Cx, a control.

The plate was washed and the retention of AF9 was determined by a colorimetric assay using streptavidin-alkaline phosphatase and pNPP as a substrate. As shown in FIG. 2A, PFWT (b) in col. 4 on the graph almost completely blocks AF9 binding. At this same peptide concentration, PFmut (a) in col. 3 also interferes with AF9 binding, but a significant amount of AF9 remains bound in the well. Peptides (c) and (d) lacking the PENETRATIN™ (Pen) transduction sequence also block AF9 binding. The 10 amino acid peptide (d) in col. 6 is the smallest molecule found to have activity in vitro. Clearly DMSO (col 2) and peptide (e) did not interfere with AF9 binding.

As shown in FIG. 2B, employing this system, PFWT causes a dose dependent reduction in the interaction between AF4 and AF9. As predicted, the AF4-AF9 interaction is abolished at 10 µg/ml PFWT. Furthermore, PFWT shows activity at a concentration as low as 10 ng/ml.

Somewhat surprisingly, and in contrast to yeast two-hybrid assays of Example 1, and the GST-pull down assay described above, the PFmut peptide also interferes to some degree with AF4-AF9 binding (data not shown). At a concentration of 20 µg/ml PFmut displaces almost 50% of the bound AF9. However, PFmut has a much lower activity that plateaus at a concentration of 40 µg/ml.

Thus, PFWT is able to disrupt AF4-AF9 complexes with high potency in vitro, while PFmut disturbs AF4-AF9 binding to a limited degree and only at high peptide concentrations.

Example 4

PFWT Disrupts AF4-AF9 Interactions In Vivo

To determine whether PFWT disrupts AF4-AF9 protein complexes in living cells, the properties of a fragment of mouse AF4 protein encompassing amino acids 623–811 (SEQ ID NO: 115) was used. The entire murine AF4 sequence can be obtained from the NCBI database at Accession Number AAD08668. This AF4R1 3A- fragment lacks the AF4 nuclear localization signal and hence is cytoplasmic when expressed alone, but is transported to the nucleus when co-expressed with AF9 (Erfurth, F., et al., 2004, cited above).

To test whether disruption of the AF4-AF9 interaction by PFWT results in delocalization of AF4R1 3A- from the nucleus to the cytoplasm even when co-expressed with exogenous AF9, the following assay was performed.

An enhanced green fluorescent protein (GFP) expression vector encoding mouse AF4 amino acids 623–811 SEQ ID NO: 115 (pEGFP-AF4R1 3A-), and a red fluorescent protein (RFP)-tagged AF9 expression vector were produced as described (Erfurth, F., et al., 2004, cited above; Srinivasan 2003, cited above; Hemenway, C. S., et al., 2001, cited above). NIH-3T3 cells were grown in chamber slides containing DMEM supplemented with 1-glutamine, 1% non-essential amino acids, 1% sodium pyruvate, 10% calf serum, and antibiotics. Cells were then transiently transfected with the expression vectors expressing fluorescent protein-tagged AF4 and AF9 using Lipofectamine™ 2000 reagent (Invitrogen). After 24 h the cells were treated with the peptides PFWT or PFmut at a concentration of 25 or 50 µg/ml and incubated overnight.

Cells on chamber slides were washed in PBS, fixed with 3% paraformaldehyde for 15 minutes, treated with 300 nM 4',6-Diamidino-2-phenyindole (DAPI) nuclear counterstain for 5 minutes, and mounted with coverslips using Prolong™ media (Molecular Probes). Slides were visualized by deconvolution fluorescence microscopy with a Leica DMRXA upright microscope (Meyer Instruments) equipped with a Sensicam™ QE CCD digital camera (Cooke Corporation) and filter sets for both EGFP (exciter HQ480/20, dichroic Q495LP, and emitter HQ510/20m) and RFP (exciter 560/55x, dichroic Q595LP, and emitter HQ645/75m). Images were captured, deconvolved, and analyzed with Slidebook™ software (Intelligent Imaging Innovations).

Image analysis entailed a pixel correlation algorithm between the EGFP and RFP fluorescence channels within each image through creation of a digital binary overlay (thresholding) over arbitrary regions in both channels. This statistical measurement determines the degree in which two pixels in an image correspond to one another. If the trend in number of pixels in both EGFP and RFP channels overlap or co-localize entirely (i.e., perfect pixel set correlation), they have an assigned correlation measurement of 1.0.

The results demonstrated that GFP-AF4R1 3A- is transported to the nucleus and localizes with AF9 when RFP-AF9 is simultaneously expressed. However, GFP-AF4R1 3A- is excluded from the nucleus and is distributed throughout the cytoplasm when co-expressed with the RFP control (gel not shown). When cells are exposed to 25 µg/ml PFWT, GFPAF4R1 3A- partially delocalizes or is displaced from RFP-AF9 (a negative correlation value). At this same concentration of PFmut, red and green pixels remain significantly positively correlated and the proteins continue to co-localize; PFmut has no observable effect. At a peptide concentration of 50 µg/ml, cells treated with PFWT reveal that GFP-AF4R1 3A- is primarily in the cytoplasm and the small amount of green fluorescence in the nucleus does not localize with RFP-AF9; little or no GFP-AF4R1 3A- remains in the nucleus despite continued expression of RFP-AF9. 50 µg/ml PFmut displaces some GFP-AF4R1 3A- from RFP-AF9 into the cytoplasm of the cells; but green fluorescence is still clearly detectable in the nucleus in a pattern that overlaps with RFP-AF9 and significant quantities of the proteins still co-localize in the nucleus.

The pixel correlation algorithm between the EGFP and RFP channels within each image was applied through creation of a digital binary overlay (thresholding) over arbitrary regions. This analysis indicates that GFP-AF4R1 3A- and RFP-AF9 are negatively correlated when measured following exposure to 50 µg/ml PFWT (i.e. red and green pixels do not overlap) but remain strongly positively correlated with exposure to PFmut (not shown).

These in vivo observations demonstrate that PFWT disrupts protein complexes comprised of a fragment of AF4 and AF9 even when the proteins have first associated within a subnuclear complex. The activity of the peptides in vivo correlates directly with their capacity to disrupt AF4-AF9 complexes in vitro. Moreover, an indirect effect of PFWT on AF4-AF9 binding, although a formal possibility, seems unlikely in light of its in vitro activity.

Example 5

PFWT Inhibits the Proliferation of Leukemia Cell Lines with T(4;11) and T(5;11) Chromosomal Translocations Evidence suggests that AF4 and AF9 act as leukemic oncoproteins when fused to MLL as a consequence of translocations at 11q23 (Ayton, P. M., and Cleary, M. L., Oncogene 2001 20: 5695–707). Although there is no established functional relationship between AF4 and AF9, the interaction between AF9 and chimeric MLL-AF4 was theorized to be is an important determinant of the malignant phenotype of leukemia with t(4;11)(q21;q23) translocations.

Having established that PFWT prevents the association of AF4 and AF9 in vitro and in vivo, the effect of the peptide on the proliferation of t(4;11) leukemia cell lines RS4;11, MV4-11, and B1 (Stong, R. C., et al., Blood 1985 65: 21–31; Lange, B., et al., Blood 1987; 70: 192–199; and Cohen, A et al., Blood 1991; 78: 94–102) was tested. These are well characterized t(4;11) leukemia cell lines and, prior to testing, expression of MLL-AF4 fusion transcripts was reconfirmed (data not shown). Additionally as a corollary to the hypothesis that PFWT inhibits leukemia cells that express MLLAF4, acute leukemia characterized by translocations at other genes encoding AF4 homologs such as LAF4 and AF5 should demonstrate similar biological behavior. Hence, the effect of PFWT was also tested on the KP-L-RY leukemia cell line, which is characterized by a t(5;11) translocation that fuses the 5' end of MLL to the 3' end of AF5 (Cohen, A et al., Blood 1991 78: 94–102.).

The t(9;11)(p22;q23) chromosomal translocation generating an MLL-AF9 fusion gene is associated with both acute myeloid and lymphoid leukemias. As PFWT is designed to disrupt the AF4-AF9 interaction, the effect of PFWT on a myelomonocytic leukemia cell line THP-1 that contains a t(9;11)(p22;q23) translocation (Tsuchiya, S., et al., Int J Cancer 1980 26: 171–176) was also tested.

Finally, as experimental controls, the effect of the peptides was tested on cell lines without 11q23 translocations, namely, MOLT-4, (T-ALL) and Reh (B-precursor ALL)

(Minowada, J., et al. J Natl Cancer Inst 1972 49: 891–5; Koziner, B., et al., Clin Immunol Immunopathol 1985 37: 135–141).

All cell lines were maintained in RPMI 1640+10% FCS. 100 μl aliquots of cell suspension ($5 \times 10^5$ cells/ml) were cultured in flat-bottomed 96 well plates in the presence of different concentrations of peptides. After 72 h incubation at 37° C. in humidified air containing 5% $CO_2$, viable cell number was determined by MTT assay as follows: 10 μl of 3-[4,5-dimethylthiazol-2-yl]-2,5-diphenyl tetrazolium bromide (MTT) (5 mg/ml concentration) (Sigma) was added to each well and incubated further for 6 h. Formazan crystals that are formed during incubation were dissolved in 100 μl of acidified isopropanol. The optical density at 550 nm (which is linearly related to the number of viable cells) was measured using a plate spectrophotometer. Growth characteristics of the leukemia cell lines were also determined for cells by Trypan Blue exclusion.

Cell viability is diminished in cell lines MV4-11, B1 and KP-L-RY, exposed to PFWT in a concentration-dependant fashion. Sensitivity to the peptide varies among the cell lines. The $LC_{50}$ of B1 cells is 20 μg/ml. Cell line RS4;11 tested similarly is more resistant (FIG. 3D); at 100 μg/ml, PFWT completely inhibits proliferation of RS4;11 cells. As predicted, PFmut inhibits cell proliferation to a lesser extent but some cell lines are nonetheless affected at high peptide concentrations. These findings correlate with the ability of PFmut to disrupt the AF4-AF9 interaction at high concentrations. As demonstrated in FIG. 3C, the KP-L-RY cell line is also inhibited by PFWT in a concentration-dependant fashion and is much less sensitive to the PFmut peptide.

Figure 3A:
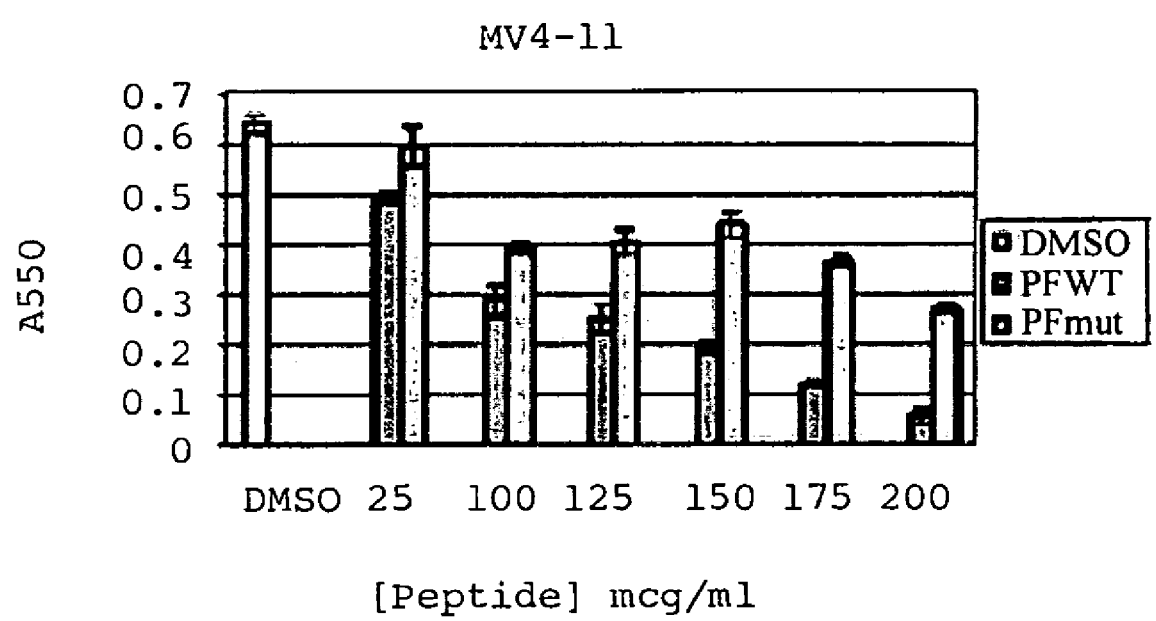
FIG. 3A is a bar graph showing that the compound PFWT inhibits leukemia cell line MV4-11 with t(4;11) and t(5;11) translocations. Cells were treated with the peptide compounds PFWT (dark bars) and PFmut (dotted bars) at differing concentrations, or vehicle (DMSO; white bar) for 72 h and viability was determined by MTT assay as described in Example 5.
Figure 3B:
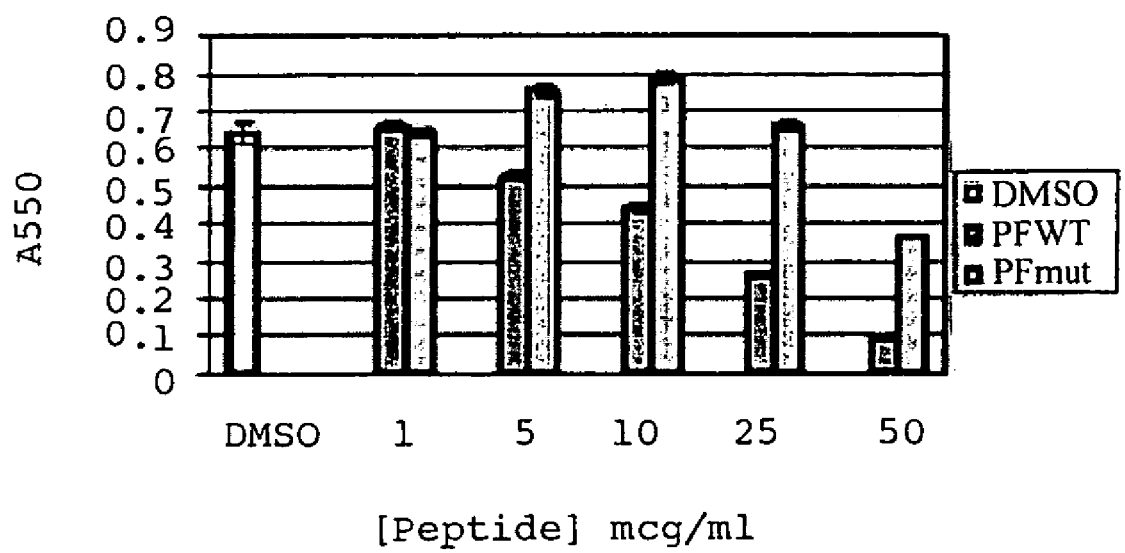
FIG. 3B is a bar graph showing that the compound PFWT inhibits leukemia cell line B1 with t(4;11) and t(5;11) translocations. Cells were treated and results illustrated as described for FIG. 3A.
Figure 3C:
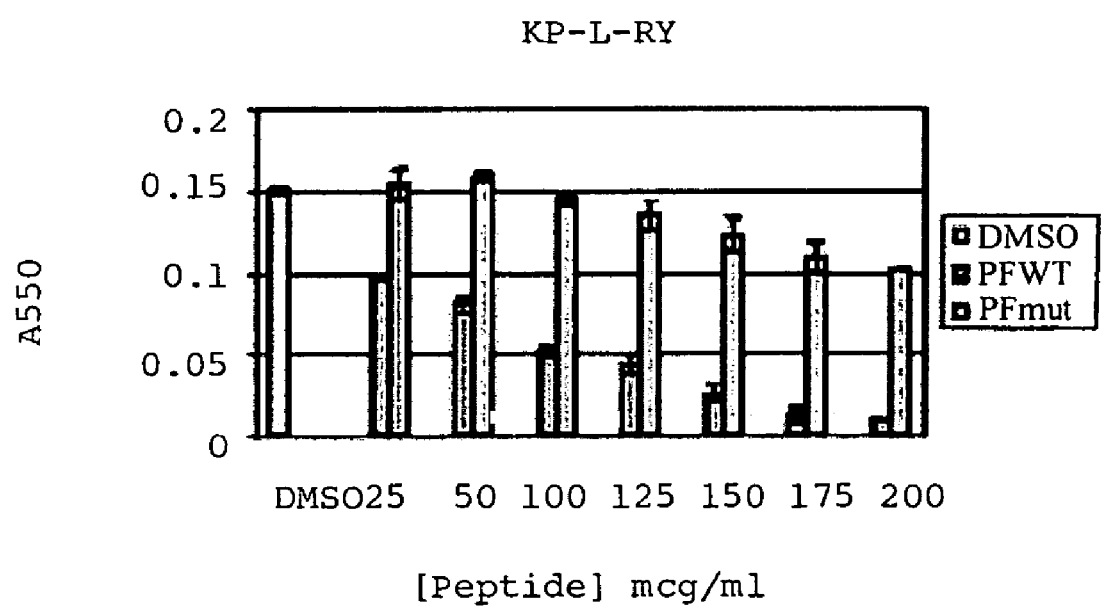
FIG. 3C is a bar graph showing that the compound PFWT inhibits leukemia cell line KP-L-RY with t(4;11) and t(5;11) translocations. Cells were treated and results illustrated as described for FIG. 3A.
Figure 3D:
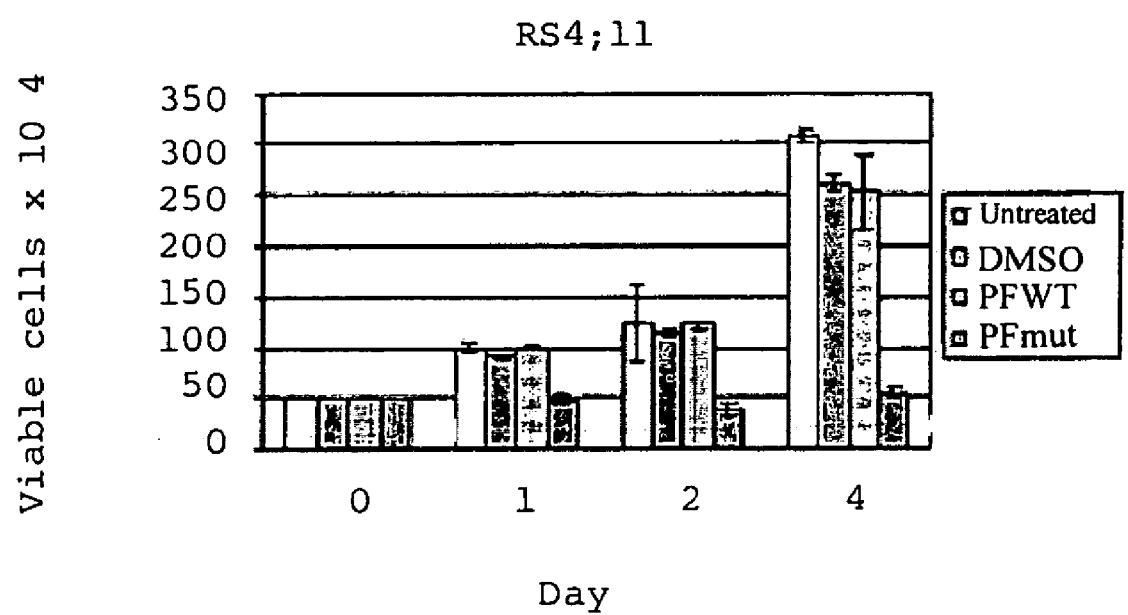
FIG. 3D is a bar graph showing that PFWT inhibits another t(4;11) leukemia cell line, RS4;11. Cells were treated with the peptide compounds PFWT (dark bars) and Pfmut (dotted bars) at 100 µg/ml, or vehicle (DMSO; light gray bar) for 72 h and viability was determined by MTT assay as described in Example 5. Untreated cells are represented by the white bars. This cell line demonstrated a poor correlation between MTT assay results and enumeration of viable cells by Trypan Blue exclusion. A growth curve illustrates that this cell line is also inhibited by PFWT.
Figure 3E:
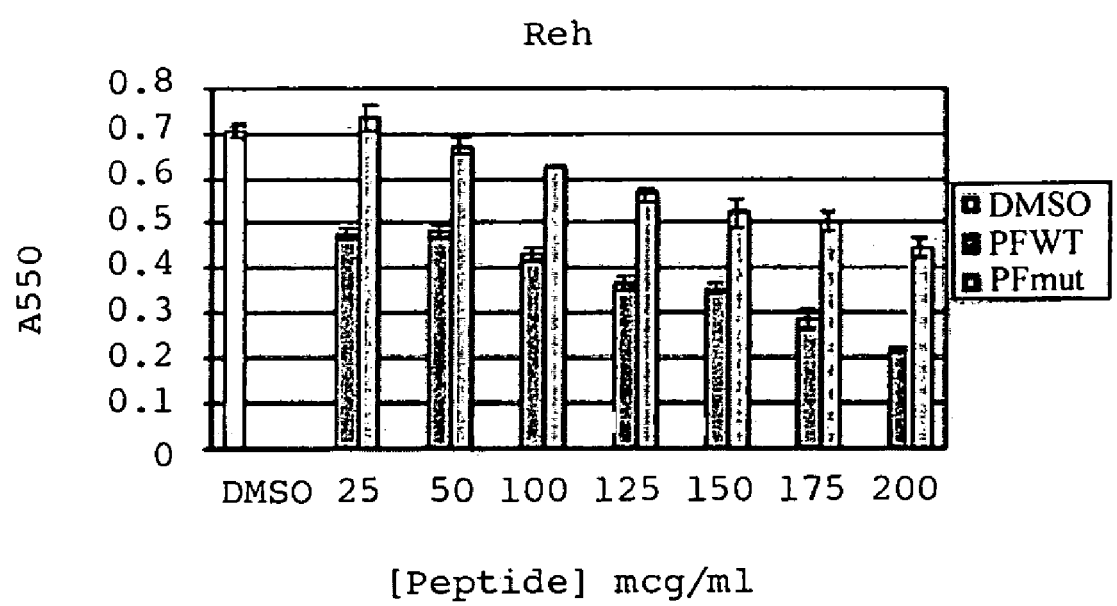
FIG. 3E is a bar graph showing that a cell line that does not contain MLL rearrangements, the B-precursor leukemia cell line, Reh is inhibited by PFWT. The cells were treated as described in FIG. 3A.
Figure 3F:
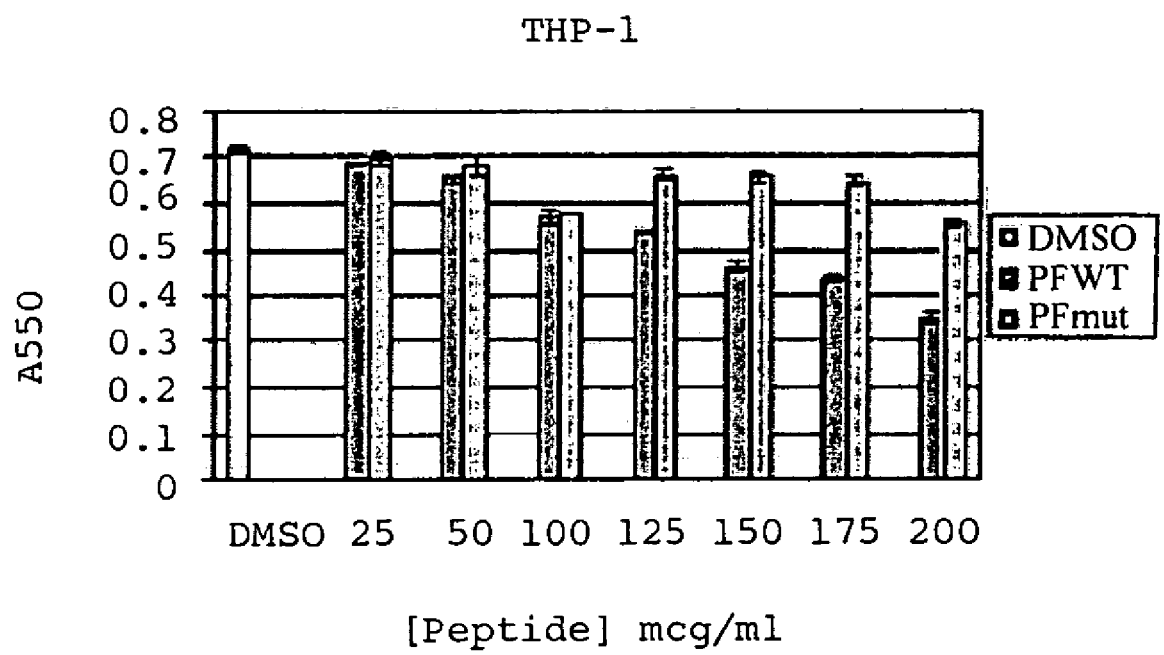
FIG. 3F is a bar graph showing that the t(9;11) leukemia cell line, THP-1, which expresses an MLL-AF9 fusion gene is not significantly inhibited by PFWT. Cells were treated with the peptide compounds PFWT (dark bars) and Pfmut (dotted bars) at varying concentrations, or vehicle (DMSO; white bar) for 72 h and viability was determined by MTT assay as described in Example 5.
Figure 3G:
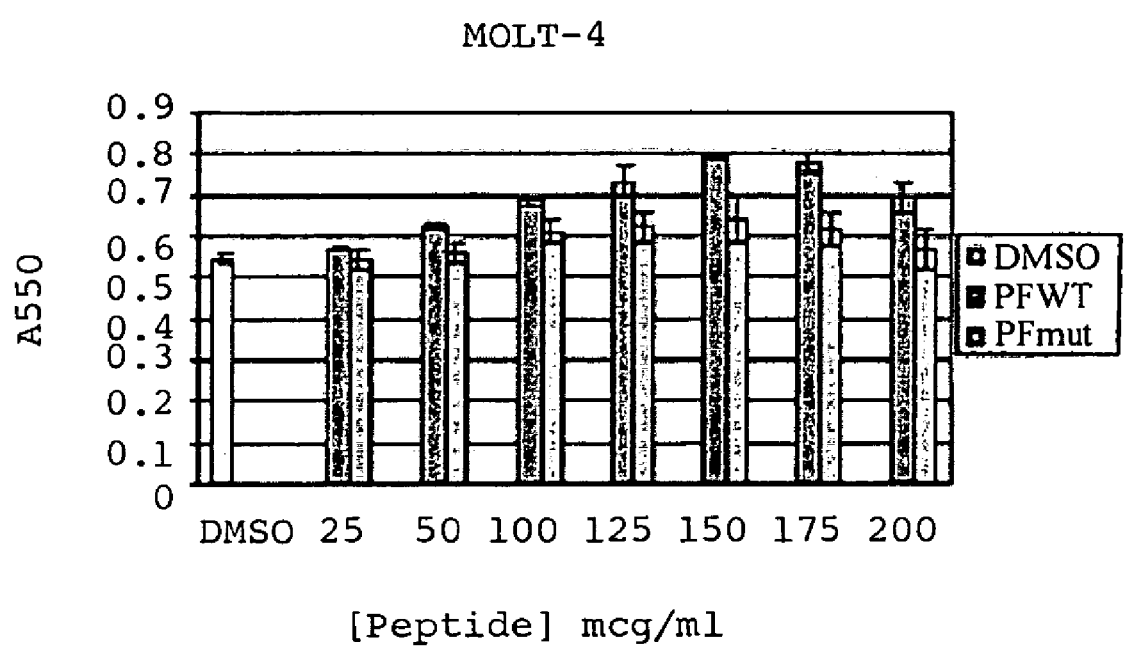
FIG. 3G is a bar graph showing that a cell line that does not contain MLL rearrangements, the T-cell leukemia line MOLT-4 is not affected by PFWT. The cells were treated as described in FIG. 3A.

MOLT-4 cells were not affected by peptide concentrations up to 200 μg/ml (FIG. 3G). Surprisingly, Reh cells that do not have any known MLL translocation are also inhibited by the peptide (FIG. 3E). This growth inhibition could be caused by the effect of the PFWT on protein complexes composed of the normal AF4 and AF9 proteins (or their homologs) that are present in the cell.

Compared to cell lines with t(4;11) or t(5;11) chromosomal translocations, THP-1 cells are inhibited to a much lesser extent and have a LC50 value of ~200 μg/ml PFWT (FIG. 3F). Either the interaction with AF4 is not required for the leukemic activity of MLL-AF9, the protein interaction is no longer necessary to maintain the malignant phenotype, or pathways involved in mediating the cytotoxic effect of PFWT are defective in THP-1 cells.

In other tests (data not shown), PFWT was found to not affect the proliferation of the Raji lymphoma cell line or the non-hematopoietic NIH 373 cell line.

Thus, proliferation of t(4;11) and t(5;11) leukemia cell lines is potently inhibited by PFWT. This inhibition is strongly linked with the ability of the peptide to disrupt AF4- (or AF5-) AF9 protein complexes.

Example 6

PFWT Triggers Apoptosis in T(4;11) Leukemia Cell Lines

The effectiveness of most chemotherapeutic agents is dependent on their ability to activate the apoptotic machinery of neoplastic cells culminating in programmed cell death (Johnstone, R. W., et al., Cell 2002; 108: 153–164). Previous studies have emphasized that t(4;11) leukemia cell lines are resistant to apoptosis (Kersey, J. H., et al., Leukemia 1998; 12: 1561–1564; Dorrie, J., et al., Leukemia 1999; 13: 15391547).

A. Annexin-V Binding Assay

To test the possibility that growth inhibition of t(4;11) leukemia cells exposed to PFWT is the result of apoptotic cell death, annexin-V labeling of the cell membrane of the leukemic cells examined in Example 5 was used to assess apoptosis as follows (Koopman, G., et al., Blood 1994 84: 1415–1420.). Annexin V binding assays were carried out using a Vibrant™ apoptosis kit (Molecular Probes). Briefly, $10^5$ the leukemic cells in 1 ml RPMI 1640 were incubated with 25 μg/ml peptide or PBS vehicle for 72 h at 37° C. in humidified air containing 5% $CO_2$. For annexin V-propidium iodide (PI) staining, cells were harvested, washed once with PBS and resuspended in 100 μl annexin binding buffer. 5 μl annexin V conjugated to Alexa Fluor 488 and 2 μl of 100 μg/ml PI were added to the cell suspension and incubated at room temperature for 15 minutes. The cells were then washed once in annexin binding buffer and resuspended in 400 μl annexin binding buffer. These samples were then analyzed by flow cytometry using Coulter benchtop flow cytometer. The cells were excited by a 488 nm wavelength laser beam and the emission was measured using a 530 nm filter for annexin V and a 575 nm filter for PI.

FIG. 3A shows that when B1 cells are treated for 24 h with PFWT, apoptosis is initiated in a substantial number of cells. Specifically, 45% of cells are in early stages of apoptosis as indicated by Annexin-V binding to the cell membrane and exclusion of PI. 35% of cells are in later stages of apoptosis characterized by cells positive for both Annexin-V and PI. A similar effect is observed with t(4;11) leukemia cell lines RS4;11 and MV4-11.

The results of the cytotoxicity assays of Example 5 (graph not shown) show that PFWT induces apoptosis in t(4;11) leukemia cells. As predicted from the results of cytotoxicity assays of Example 5, MOLT-4 cells are comparatively resistant to the effects of PFWT (Table 7).

TABLE 7 t(4;11) leukemia cell lines RS4;11 and MV4-11 undergo apoptosis when exposed to PFWT. The T-cell ALL cell line MOLT-4 is relatively resistant to PFWT-induced apoptosis.

| | % Total apoptotic cells (% early apoptotic cells) | | |
| --- | --- | --- | --- |
| Cell line | DMSO 1 μl/ml | PF mut 50 μg/ml | PFWT 50 μg/ml |
| MV4-11 | 16.2 (8.22) | 23.16 (8.26) | 45.3 (28.42) |
| RS4;11 | 5.76 (1.22) | 7.22 (1.36) | 34.64 (26.18) |
| MOLT-4 | 6.36 (2) | 6.64 (1.36) | 18.8 (11.64) |

B. Caspace Assays

To examine an additional marker of apoptosis, apoptosis assays utilizing the FITC-labeled VAD-FMK caspase substrate, CaspACE FITC-VAD-FMK (Promega) were performed according to the manufacturer's instructions. Caspase activation in individual cells was monitored by binding of the caspase substrate, followed by flow cytometry analysis. Briefly, B1 leukemia cells were suspended in RPMI 1640+10% FCS at a concentration of 5×10$^5$ cells/ml and treated with 50 μg PFWT, PFmut or an equal volume of DMSO. Following an overnight incubation at 37° C., the fluorescent caspase substrate CaspACE FITC-VAD-FMK marker was added to a final concentration of 10 μM and incubated for 20 minutes at 37° C. under light protective conditions. The cells were pelletted, washed, and resuspended in PBS. Cells were then analyzed by flow cytometry using a Becton Dickinson FACS Vantage flow cytometer. A 488 nm wavelength argon-ion laser beam was used for excitation, and the emission was measured using a 530 nm filter.

The results show by an increase in fluorescence intensity in B1 cells treated with PFWT that caspases are activated in B1 t(4;11) leukemia cells exposed to PFWT for 24 h. In contrast, little caspase activation can be detected by this method in cells treated with the "inactive" peptide, PFmut, or the peptide vehicle, DMSO. Thus two distinct indicators of apoptosis, cell membrane phosphatidyl serine translocation and caspase activation are detected in B1 cells treated with PFWT.

C. Cell Cycle Analysis

Leukemia cells were subjected to cell cycle analyses using a Cellular DNA flow cytrometric analysis kit (Roche) according to manufacturers' protocols to determine if PFWT might also induce cell cycle arrest. B1 cells were treated with peptides as outlined above and fixed. For DNA staining, cells were harvested and washed and resuspended with PBS at a concentration of 10$^6$ cells/ml. 1 unit/ml of RNase and 50 μg/ml of PI was added to this suspension and incubated at 37° C. for 1 hr and analyzed by flow cytometry using Coulter benchtop flow cytometer.

The proportion of cells in G1, S, and G2 was 41:51:8 for DMSO, 52:40:8 for PFmut, and 47:45:8 for PFWT. In contrast, the appearance of a large sub-G1 population of cells treated with PFWT (51% of all events) is consistent with nuclear fragmentation and apoptotic cell death and independently supports the conclusion that PFWT induces apoptosis in B1 cells (data not shown).

Example 7

PFWT Does Not Affect the Colony Forming Potential of Hematopoietic Progenitor Cells A. Clonogenic Assays PFWT is toxic to several leukemia cell lines raising the possibility that normal hematopoietic cells are also sensitive to the peptide. To verify whether PFWT has any effect on hematopoietic stem cells, standard methylcellulose-based assays were employed to enumerate the colony-forming potential of human peripheral blood and bone marrow stem cells.

Cryopreserved bone marrow and peripheral blood hematopoietic progenitor cells from healthy donors were thawed and diluted with M199 media (Invitrogen) to give a final DMSO concentration of 0.1%. Cells were incubated at room temperature for 2 h for equilibration. Nucleated cells at a concentration of 5×10$^5$ cells/ml were then incubated with the peptides PFWT or PFmut or DMSO control vehicle for 48 or 72 h. After the incubation period, 400 μl of the cell suspensions were suspended in 3.6 ml MethoCult GF H4434 methylcellulose media containing cytokines (erythropoietin, G-CSF, GM-CSF, stem cell factor, IL-3 and IL-6) (Stem Cell Technologies) and transferred to 25 mm plates with grids. The cells were plated in triplicate and incubated for 2 weeks at 37° C. with 5% CO$_2$ in a humidified incubator. After 2 weeks, the number of colonies (>50 cells) per plate was counted under an inverted light microscope as a measure of progenitor cell viability.

Figure 4A:
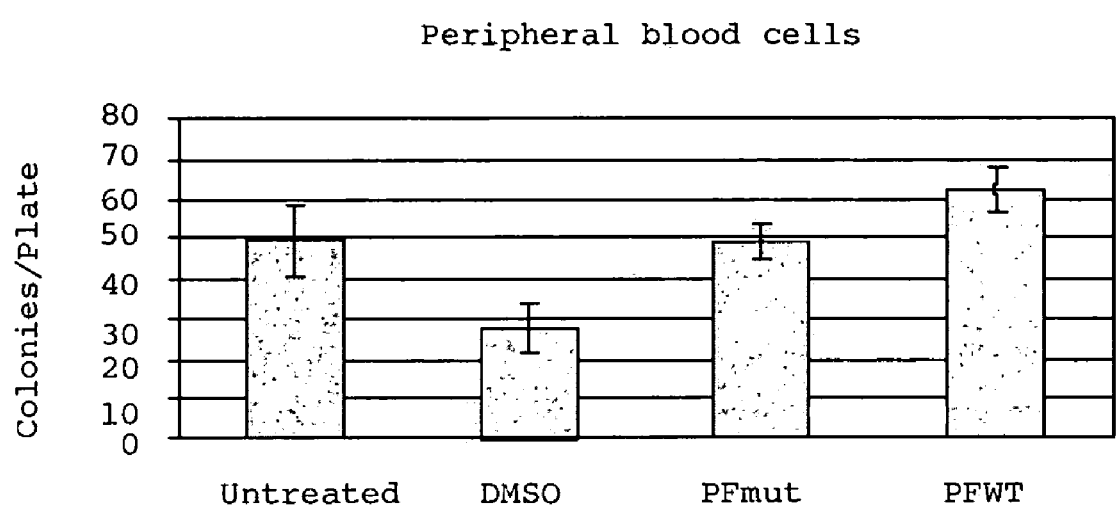
FIG. 4A is a bar graph showing that hematopoietic progenitor cells, i.e., peripheral blood (stem) cells, readily accumulate PFWT but the peptide does not impair their colony forming potential. Cells were incubated with 100 μg/ml PFWT, PFmut, DMSO vehicle for 72 h and plated in methylcellulose medium containing growth factors. The number of colonies greater than 50 cells was counted after 14 days. There was a small reduction in the colony count in the sample treated with DMSO vehicle, but PFWT does have any effect on the number of colonies formed per plate.

The results indicate that neither PFWT nor PFmut have any significant effect on the numbers or proliferative capacity of hematopoietic progenitor cells at a peptide concentration of 100 μg/ml (FIG. 4A). At higher concentrations, toxicity was observed as a consequence of the DMSO vehicle and we were unable to draw conclusions about effects specifically attributable to the peptide. Nevertheless, hematopoietic progenitor cells appear to be resistant to the PFWT peptide at concentrations that inhibit t(4;11) leukemia cell lines.

B. Peptide Uptake Assays

To assess the possibility that the resistance of hematopoietic progenitor cells to PFWT is due to limited uptake of the peptide, uptake of fluorescein-conjugated PFWT was investigated. PFWT peptide was conjugated to fluorescein at the N-terminus. This flourescein-tagged peptide was synthesized by United Biochemicals (Seattle, Wash.) and purified to >85% by high pressure liquid chromatography.

To measure peptide uptake, leukemia cells sensitive to PFWT (B1), resistant leukemia cells (MOLT-4), and CD34$^+$-selected hematopoietic cells (>90% CD34$^+$) were incubated at 37° C. for 30 min in serum-free RPMI 1640. The sample was divided and fluorescein-tagged PFWT was added to the experimental group of cells to a final concentration of 45 μg/ml peptide. An equal volume of PBS was added to the control group of cells. Cells were incubated an additional 30 min followed by the addition of trypsin/EDTA to a final concentration of 0.125% trypsin to eliminate peptide adherent to the outer surface of the cell membrane. After incubation for 10 min at 37° C. in trypsin-containing serum-free medium, cells were washed once and resuspended in PBS. Fluorescence was then measured by flow cytometry using a Becton Dickinson FACS Vantage flow cytometer (Richard, J. P., et al., J Biol Chem 2003; 278: 585–590). A 488 nm wavelength argon-ion laser beam was used for excitation, and the emission was measured using a 530 nm filter.

Figure 4B:
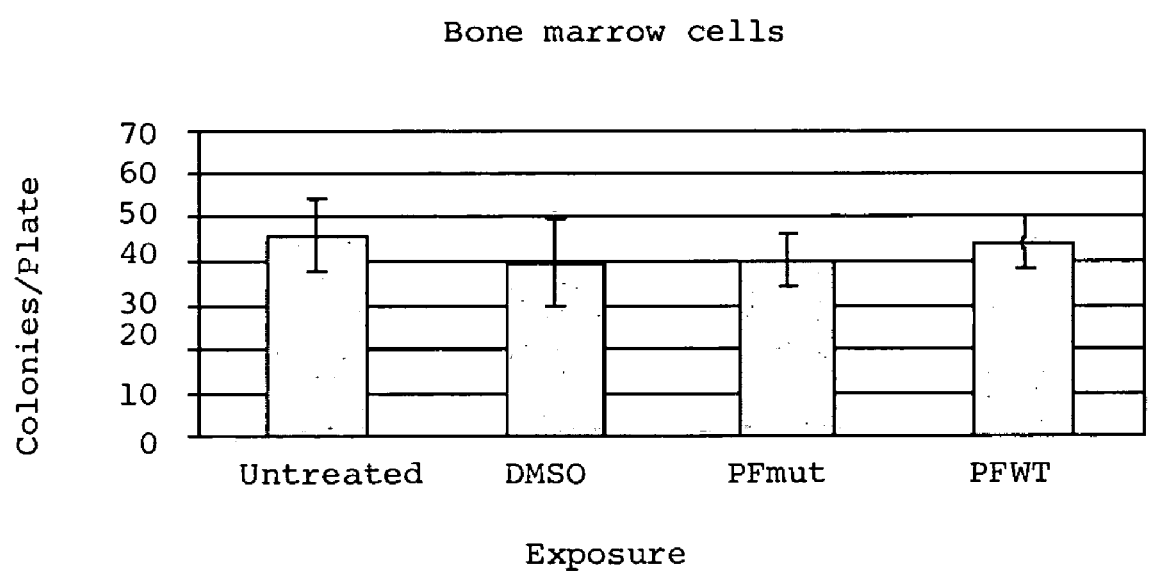
FIG. 4B is a bar graph showing that bone marrow (stem) cells were incubated with 100 μg/ml PFWT, PFmut, or DMSO vehicle for 48 h and analyzed as in FIG. 4A.

FIG. 4A–4B show that B1 and MOLT-4 leukemia cells exhibit a 10-fold increase in fluorescence after treatment with the labeled peptide. This increase is consistent with intracellular accumulation of fluorescein-conjugated PFWT. Under the same assay conditions, CD34$^+$-selected hematopoietic cells show a dramatic 100-fold increase in fluorescence indicating that fluorescein-conjugated PFWT is readily transported into these cells. Compared to the PFWT-sensitive leukemia cell line B1, CD34$^+$ cells accumulate almost 10-fold more peptide based on this assay. MOLT-4 leukemia cells are resistant to PFWT but show no difference in the accumulation of labeled PFWT when compared to B1 cells (data not shown). This experiment indicates that the resistance of hematopoietic progenitor cells to PFWT is not the result of diminished accumulation of the peptide relative to other cell types.

All documents and public databases cited within this specification are incorporated herein by reference.

The invention claimed is:

1. A compound of the formula

R1-Leu-A2-Val-A4-Ile-A6-Leu-A8-A9-A10-R2
(SEQ ID NO: 1)

or a salt thereof,
wherein A2, A9 and A10 are selected independently from the group consisting of a hydrophobic amino acid which is naturally occurring in proteins or non-naturally occurring in proteins;

wherein A4 is a positively charged amino acid which is naturally occurring in proteins or non-naturally occurring in proteins;

wherein A6 and A8 are selected independently from the group consisting of any naturally occurring or non-naturally occurring amino acid;

wherein R1 is an optional moiety selected from the group consisting of H, a straight chain, branched, cyclic or heterocyclic $C_{1-12}$ alkyl group, a straight chain, branched, cyclic or heterocyclic $C_{1-12}$ alkanoyl group, a sequence of one to 5 additional naturally occurring or non-naturally occurring amino acids, a spacer capable of cyclizing the peptide by bridging between the N- and C- termini thereof, an acidic moiety, and a penetration enhancer; and wherein R2 is selected from the group consisting of H, OH, $CO_2H$, $CONH_2$, an imide group, a sugar, a straight chain, branched, cyclic or heterocyclic $C_{1-12}$ alkyl group; a straight chain, branched, cyclic or heterocyclic $C_{1-12}$ alkanoyl group; an amide, imide or sugar substituted with at least one of said alkyl or alkanoyl groups, a sequence of one to 5 additional naturally occurring or non-naturally occurring amino acids, and a spacer capable of cyclizing the compound by bridging between the N- and C-termini thereof.

2. The compound according to claim 1, wherein A4 is selected from the group consisting of Lys, Arg and His.

3. The compound according to claim 1, wherein A6 and A8 are selected from the group consisting of Ala, Arg, Asn, Asp, Cys, Gln, Glu, Gly, His, Ile, Leu, Lys, Met Phe, Pro, Ser, Thr, Trp, Tyr, and Val.

4. The compound according to claim 1, wherein A2, A9 and A10 are independently selected from Val, Trp, Ile, Leu, Met, Phe, Tyr, and a non-naturally-occuring amino acid that is resistant to degradation by mammalian enzymes.

5. The compound according to claim 1, wherein one or more of said amino acids in said formula are D-amino acids.

6. The compound according to claim 1, wherein one or more of said amino acids in said formula contain substitutions for the alpha-carbon in the amino acid structure.

7. The compound according to claim 1, wherein one or more of said amino acids in said formula contains a beta-carbon in its amino acid structure.

8. The compound according to claim 1, wherein one or more of said amino acids is an amide substituted amino acid.

9. The compound according to claim 1, wherein one or more of said amino acids is substituted with a straight chain, branched, cyclic or heterocyclic $C_{1-12}$ alkyl group, a straight chain, branched, cyclic, or heterocyclic $C_{1-12}$ alkanoyl group.

10. An isolated peptide selected from the group consisting of R1-Leu-Met-Val-Lys-Ile-Thr-Leu-Asp-Leu-Leu (SEQ ID NO: 8), or R1-Leu-Met-Val-Lys-Ile-Thr-Leu-Asp-Leu-Leu-Ser-Arg-Ile-Pro (SEQ ID NO: 14), and R1-Leu-Trp-Val-Lys-Ile-Asp-Lcu-Asp-Leu-Leu-Ser-Arg-Val (SEQ ID NO: 27), wherein R1 is an optional moiety selected from the group consisting of H, a straight chain, branched, cyclic or heterocyclic $C_{1-12}$ alkyl group, a straight chain, branched, cyclic or heterocyclic $C_{1-12}$ alkanoyl group, a sequence of one to 5 additional naturally occurring or non-naturally occurring amino acids, a spacer capable of cyclizing the peptide by bridging between the N- and C-termini thereof, an acidic moiety, and a penetration enhancer.

11. The compound according to claim 1, comprising at least two peptides of said formula, wherein the second peptide is attached to any amino acid of the first peptide.

12. A composition comprising one or more of the compounds of claim 1 in a carrier.

13. The composition according to claim 12, further comprising a liposome.

14. A compound of the formula

R1-Leu-A2-Val-A4-Ile-A6-Leu-A8-A9-A10-R2
(SEQ ID NO: 1)

or a salt thereof, wherein A2 is Met or Trp;

wherein A9 and A10 are selected independently from the group consisting of a hydrophobic amino acid which is naturally occurring in proteins or non-naturally occurring in proteins;

wherein A4 is a positively charged amino acid which is naturally occurring in proteins or non-naturally occurring in proteins;

wherein A6 and A8 are selected independently from the group consisting of any naturally occurring or non-naturally occurring amino acid;

wherein R1 is an optional moiety selected from the group consisting of H, a straight chain, branched, cyclic or heterocyclic $C_{1-12}$ alkyl group, a straight chain, branched, cyclic or heterocyclic $C_{1-12}$ alkanoyl group, a sequence of one to 5 additional naturally occurring or non-naturally occurring amino acids, a spacer capable of cyclizing the peptide by bridging between the N- and C-termini thereon an acidic moiety, and a penetration enhancer; and wherein R2 is selected from the group consisting of H, OH, $CO_2H$, $CONH_2$, an imide group, a sugar, a straight chain, branched, cyclic or heterocyclic $C_{1-12}$ alkyl group; a straight chain, branched, cyclic or heterocyclic $C_{1-12}$ alkanoyl group; an amide, imide or sugar substituted with at least one of said alkyl or alkanoyl groups, a sequence of one to 5 additional naturally occurring or non-naturally occurring amino acids, and a spacer capable of cyclizing the compound by bridging between the N- and C-termini thereof.

15. The compound according to claim 14, wherein

A4 is Lys;

A6 is Thr or Asp;

A8 is Asp;

A9 and A10 are each Leu;

R1 is H; and

R2 is H or a sequence of one to 4 additional naturally occurring or non-naturally occurring amino acids.

16. A compound of the formula

R1-Leu-A2-Val-A4-Ile-A6-Leu-A8-A9-A10-R2
(SEQ ID NO: 1)

or a salt thereof, wherein A2, A9 and A10 are selected independently from the group consisting of a hydrophobic amino acid which is naturally occurring in proteins or non-naturally occurring in proteins;

wherein A4 is a positively charged amino acid which is naturally occurring in proteins or non-naturally occurring in proteins;

wherein A6 and A8 are selected independently from the group consisting of any naturally occurring or non-naturally occurring amino acid;

wherein R1 is an optional moiety selected from the group consisting of H, a straight chain, branched, cyclic or heterocyclic $C_{1-12}$ alkyl group, a straight chain, branched, cyclic or heterocyclic $C_{1-12}$ alkanoyl group, a sequence of one to 5 additional naturally occurring or non-naturally occurring amino acids, a spacer capable of cyclizing the peptide by bridging between the N- and C-termini thereon an acidic moiety, and a penetration enhancer; and wherein R2 is H.

* * * * *

UNITED STATES PATENT AND TRADEMARK OFFICE
CERTIFICATE OF CORRECTION

PATENT NO. : 7,189,691 B2
APPLICATION NO. : 11/094595
DATED : March 13, 2007
INVENTOR(S) : Hemenway It is certified that error appears in the above-identified patent and that said Letters Patent is hereby corrected as shown below:

Col. 1, line 8, replace "60/558,458" with -- 60/558,456 --.

Col. 1, line 67, replace "247253" with -- 247-253 --.

Col. 2, line 14, replace "$CD10^{31}$" with -- $CD10^-$ --.

Col. 2, line 52, replace "776784" with -- 776-784 --.

Col. 5, line 16, replace "does" with -- does not --.

Col. 5, line 31, replace "Ila" with -- Ile --.

Col. 7, line 6, replace "may" with -- may be --.

Col. 7, line 16, replace "Gin" with -- Gln --.

Col. 9, line 10, replace "or or" with -- or --.

Col. 16, line 47, replace "or" with -- of --.

Col. 18, line 56, replace "nad/or" with -- and/or --.

Col. 18, line 56, replace "dthe" with -- the --.

Col. 20, line 47, replace "compounds" with -- compound --.

Col. 21, line 43, delete "to".

Col. 21, line 67, replace "8:4447" with -- 8:44-47 --.

Col. 23, line 19, replace "60" with -- $\alpha$ --.

Col. 24, line 21, replace "Lue9" with -- Leu9 --.

Col. 24, line 59, replace "attenuate" with -- attenuated --.

Col. 25, line 10, replace "additional" with -- addition --.

Col. 25, line 32, replace "coupled" with -- coupling --.

UNITED STATES PATENT AND TRADEMARK OFFICE
CERTIFICATE OF CORRECTION

PATENT NO. : 7,189,691 B2
APPLICATION NO. : 11/094595
DATED : March 13, 2007
INVENTOR(S) : Hemenway It is certified that error appears in the above-identified patent and that said Letters Patent is hereby corrected as shown below:

Col. 28, line 30, replace "T(4;11) and T(5;11)" with -- T(4:11) and T(5:11) --.

Col. 28, line 39, delete "is".

Col. 28, line 40, replace "t(4;11)(q21;q23)" with -- t(4:11)(q21:q23) --.

Col. 30, line 6, replace "15391547" with -- 1539-1547 --.

Col. 85, line 46, replace "Lys-Ile-Asp-Lcu-Asp-Leu-Leu-Ser-Arg-Val" with

-- Lys-Ile-Asp-Leu-Asp-Leu-Leu-Ser-Arg-Val --.

Col. 86, line 20, replace "thereon" with -- thereof --.

Signed and Sealed this

Fourteenth Day of August, 2007

JON W. DUDAS
*Director of the United States Patent and Trademark Office*

SEQUENCE LISTING

<160> NUMBER OF SEQ ID NOS: 118

<210> SEQ ID NO 1
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members
<220> FEATURE:
<221> NAME/KEY: MISC_FEATURE
<222> LOCATION: (1)..(1)
<223> OTHER INFORMATION: Leu in position 1 can be selectively modified
      by any of the R1 group of amino acids or compounds
<220> FEATURE:
<221> NAME/KEY: MISC_FEATURE
<222> LOCATION: (2)..(2)
<223> OTHER INFORMATION: is a hydrophobic amino acid
<220> FEATURE:
<221> NAME/KEY: MISC_FEATURE
<222> LOCATION: (4)..(4)
<223> OTHER INFORMATION: is a positively charged amino acid
<220> FEATURE:
<221> NAME/KEY: MISC_FEATURE
<222> LOCATION: (6)..(6)
<223> OTHER INFORMATION: can be any amino acid
<220> FEATURE:
<221> NAME/KEY: MISC_FEATURE
<222> LOCATION: (8)..(8)
<223> OTHER INFORMATION: can be any amino acid
<220> FEATURE:
<221> NAME/KEY: MISC_FEATURE
<222> LOCATION: (9)..(9)
<223> OTHER INFORMATION: is a hydrophobic amino acid
<220> FEATURE:
<221> NAME/KEY: MISC_FEATURE
<222> LOCATION: (10)..(10)
<223> OTHER INFORMATION: is a hydrophobic amino acid
<220> FEATURE:
<221> NAME/KEY: MISC_FEATURE
<222> LOCATION: (10)..(10)
<223> OTHER INFORMATION: any of the amino acids in position 10 can be
      selectively modified by any of the R2 group of amino acids or
      compounds

<400> SEQUENCE: 1

Leu Xaa Val Xaa Ile Xaa Leu Xaa Xaa Xaa
1               5                   10

<210> SEQ ID NO 2
<211> LENGTH: 14
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 2

Leu Trp Val Lys Ile Asp Leu Asp Leu Leu Ser Arg Val Pro
1               5                   10

<210> SEQ ID NO 3
<211> LENGTH: 14
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 3

```
Leu Trp Glu Lys Ser Asp Leu Asp Leu Leu Ser Arg Val Pro
1               5                   10
```

<210> SEQ ID NO 4
<211> LENGTH: 26
<212> TYPE: PRT
<213> ORGANISM: Artificial Sequence
<220> FEATURE:
<223> OTHER INFORMATION: structurally based on a fragment of the
      naturally occuring human and murine AF4 protein family members
<220> FEATURE:
<221> NAME/KEY: DISULFID
<222> LOCATION: (1)..(26)
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (26)..(26)
<223> OTHER INFORMATION: AMIDATION

<400> SEQUENCE: 4

```
Cys Leu Ile Val Lys Ile Ala Leu Ala Leu Leu Gly Pro Ala Gly Leu
1               5                   10                  15

Ile Val Lys Ile Ala Leu Ala Leu Leu Cys
            20                  25
```

<210> SEQ ID NO 5
<211> LENGTH: 20
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 5

```
Lys Lys Lys Lys Lys Lys Arg Lys Val Leu Ile Val Arg Ile Asp Leu
1               5                   10                  15

Asp Leu Leu Ser
            20
```

<210> SEQ ID NO 6
<211> LENGTH: 5
<212> TYPE: PRT
<213> ORGANISM: Artificial Sequence
<220> FEATURE:
<223> OTHER INFORMATION: synthetic sequence with a net positive charge

<400> SEQUENCE: 6

```
Lys Val Asp Leu Val
1               5
```

<210> SEQ ID NO 7
<211> LENGTH: 4
<212> TYPE: PRT
<213> ORGANISM: Artificial Sequence
<220> FEATURE:
<223> OTHER INFORMATION: synthetic sequence with a net positive charge
<220> FEATURE:
<221> NAME/KEY: MOD_RES
<222> LOCATION: (1)..(1)
<223> OTHER INFORMATION: ACETYLATION

<400> SEQUENCE: 7

```
Lys Lys Lys Lys
1
```

```
<210> SEQ ID NO 8
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 8

Leu Met Val Lys Ile Thr Leu Asp Leu Leu
1               5                   10

<210> SEQ ID NO 9
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 9

Leu Leu Ala Leu Ala Ile Lys Val Ile Leu
1               5                   10

<210> SEQ ID NO 10
<211> LENGTH: 4
<212> TYPE: PRT
<213> ORGANISM: Artificial Sequence
<220> FEATURE:
<223> OTHER INFORMATION: structurally based on a fragment of the
      naturally occuring human and murine AF4 protein family members
<220> FEATURE:
<221> NAME/KEY: MISC_FEATURE
<222> LOCATION: (3)..(3)
<223> OTHER INFORMATION: can be Ile or Val

<400> SEQUENCE: 10

Ser Arg Xaa Pro
1

<210> SEQ ID NO 11
<211> LENGTH: 9
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 11

Lys Lys Lys Lys Lys Lys Arg Lys Val
1               5

<210> SEQ ID NO 12
<211> LENGTH: 6
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 12

Lys Lys Lys Arg Lys Val
1               5

<210> SEQ ID NO 13
<211> LENGTH: 10
<212> TYPE: PRT
<213> ORGANISM: Artificial Sequence
```

```
<220> FEATURE:
<223> OTHER INFORMATION: structurally based on a fragment of the
      naturally occuring human and murine AF4 protein family members

<400> SEQUENCE: 13

Leu Ile Val Lys Ile Ala Leu Ala Leu Leu
1               5                   10

<210> SEQ ID NO 14
<211> LENGTH: 14
<212> TYPE: PRT
<213> ORGANISM: Artificial Sequence
<220> FEATURE:
<223> OTHER INFORMATION: a fragment of the naturally occuring human AF4
      protein

<400> SEQUENCE: 14

Leu Met Val Lys Ile Thr Leu Asp Leu Leu Ser Arg Ile Pro
1               5                   10

<210> SEQ ID NO 15
<211> LENGTH: 14
<212> TYPE: PRT
<213> ORGANISM: Artificial Sequence
<220> FEATURE:
<223> OTHER INFORMATION: a fragment of the naturally occuring human AF4
      protein

<400> SEQUENCE: 15

Leu Val Val Lys Ile Thr Leu Asp Pro Leu Thr Arg Ile Pro
1               5                   10

<210> SEQ ID NO 16
<211> LENGTH: 14
<212> TYPE: PRT
<213> ORGANISM: Artificial Sequence
<220> FEATURE:
<223> OTHER INFORMATION: a fragment of the naturally occuring human LAF4
      protein

<400> SEQUENCE: 16

Leu Trp Val Lys Ile Asp Leu Thr Leu Leu Ser Arg Ile Pro
1               5                   10

<210> SEQ ID NO 17
<211> LENGTH: 14
<212> TYPE: PRT
<213> ORGANISM: Artificial Sequence
<220> FEATURE:
<223> OTHER INFORMATION: a fragment of the naturally occuring human AF5
      protein

<400> SEQUENCE: 17

Leu Ile Val Lys Ile Asp Leu Asn Leu Leu Thr Arg Ile Pro
1               5                   10

<210> SEQ ID NO 18
<211> LENGTH: 14
<212> TYPE: PRT
<213> ORGANISM: Artificial Sequence
<220> FEATURE:
<223> OTHER INFORMATION: a fragment of the naturally occuring murine
      FMR2 protein

<400> SEQUENCE: 18

Leu Trp Val Lys Ile Asp Leu Asp Leu Leu Ser Arg Val Pro
1               5                   10
```

-continued

```
<210> SEQ ID NO 19
<211> LENGTH: 14
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 19

Leu Met Val Lys Ile Thr Leu Asp Leu Leu Ser Arg Ile Pro
1               5                   10

<210> SEQ ID NO 20
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 20

Leu Met Val Arg Ile Thr Leu Asp Leu Leu
1               5                   10

<210> SEQ ID NO 21
<211> LENGTH: 11
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 21

Leu Met Ile Lys Ile Thr Leu Asp Leu Leu Ser
1               5                   10

<210> SEQ ID NO 22
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 22

Leu Phe Val Lys Ile Thr Leu Asp Leu Leu
1               5                   10

<210> SEQ ID NO 23
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 23

Leu Phe Val His Ile Thr Leu Asp Leu Leu
1               5                   10

<210> SEQ ID NO 24
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members
```

-continued

```
<400> SEQUENCE: 24

Leu Phe Val Arg Ile Thr Leu Asp Leu Leu
1               5                   10

<210> SEQ ID NO 25
<211> LENGTH: 11
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 25

Leu Ile Val Lys Ile Thr Leu Asp Leu Leu Ser
1               5                   10

<210> SEQ ID NO 26
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 26

Leu Ile Val Arg Ile Thr Leu Asp Leu Leu
1               5                   10

<210> SEQ ID NO 27
<211> LENGTH: 13
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 27

Leu Trp Val Lys Ile Asp Leu Asp Leu Leu Ser Arg Val
1               5                   10

<210> SEQ ID NO 28
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 28

Leu Met Val Arg Ile Thr Leu Asp Met Leu
1               5                   10

<210> SEQ ID NO 29
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 29

Leu Met Val His Ile Thr Leu Asp Met Leu
1               5                   10

<210> SEQ ID NO 30
<211> LENGTH: 10
<212> TYPE: PRT
```

```
<213> ORGANISM: Artificial Sequence
<220> FEATURE:
<223> OTHER INFORMATION: structurally based on a fragment of the
      naturally occuring human and murine AF4 protein family members

<400> SEQUENCE: 30

Leu Phe Val Lys Ile Thr Leu Asp Leu Met
1               5                   10

<210> SEQ ID NO 31
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 31

Leu Phe Val His Ile Thr Leu Asp Leu Met
1               5                   10

<210> SEQ ID NO 32
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 32

Leu Phe Val Arg Ile Thr Leu Asp Leu Met
1               5                   10

<210> SEQ ID NO 33
<211> LENGTH: 11
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 33

Leu Ile Val Glu Ile Thr Leu Asp Leu Leu Ser
1               5                   10

<210> SEQ ID NO 34
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 34

Leu Ile Val Arg Ile Thr Leu Asp Phe Leu
1               5                   10

<210> SEQ ID NO 35
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 35

Leu Ile Val His Ile Thr Leu Asp Phe Leu
1               5                   10
```

<210> SEQ ID NO 36
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 36

Leu Met Val Lys Ile Thr Leu Asp Leu Leu
1               5                   10

<210> SEQ ID NO 37
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 37

Leu Ile Val His Ile Thr Leu Asp Leu Leu
1               5                   10

<210> SEQ ID NO 38
<211> LENGTH: 11
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 38

Leu Leu Val Lys Ile Thr Val Asp Leu Leu Ser
1               5                   10

<210> SEQ ID NO 39
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 39

Leu Leu Val His Ile Thr Leu Asp Leu Leu
1               5                   10

<210> SEQ ID NO 40
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 40

Leu Leu Val Arg Ile Thr Leu Asp Leu Leu
1               5                   10

<210> SEQ ID NO 41
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

```
<400> SEQUENCE: 41

Leu Trp Val Lys Ile Thr Leu Asp Leu Leu
1               5                   10

<210> SEQ ID NO 42
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 42

Leu Trp Val His Ile Thr Leu Asp Leu Leu
1               5                   10

<210> SEQ ID NO 43
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 43

Leu Trp Val Arg Ile Thr Leu Asp Leu Leu
1               5                   10

<210> SEQ ID NO 44
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 44

Leu Tyr Val Lys Ile Thr Leu Asp Leu Leu
1               5                   10

<210> SEQ ID NO 45
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 45

Leu Tyr Val His Ile Thr Leu Asp Leu Leu
1               5                   10

<210> SEQ ID NO 46
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 46

Leu Tyr Val Arg Ile Thr Leu Asp Leu Leu
1               5                   10

<210> SEQ ID NO 47
<211> LENGTH: 10
```

-continued

<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 47

Leu Val Val Lys Ile Thr Leu Asp Leu Leu
1               5                   10

<210> SEQ ID NO 48
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 48

Leu Val Val His Ile Thr Leu Asp Leu Leu
1               5                   10

<210> SEQ ID NO 49
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 49

Leu Val Val Arg Ile Thr Leu Asp Leu Leu
1               5                   10

<210> SEQ ID NO 50
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 50

Leu Val Val Lys Ile Thr Leu Asp Tyr Leu
1               5                   10

<210> SEQ ID NO 51
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 51

Leu Val Val His Ile Thr Leu Asp Tyr Leu
1               5                   10

<210> SEQ ID NO 52
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 52

Leu Val Val Arg Ile Thr Leu Asp Tyr Leu
1               5                  10

<210> SEQ ID NO 53
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 53

Leu Val Val Lys Ile Thr Leu Asp Leu Tyr
1               5                  10

<210> SEQ ID NO 54
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 54

Leu Val Val His Ile Thr Leu Asp Leu Tyr
1               5                  10

<210> SEQ ID NO 55
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 55

Leu Val Val Arg Ile Thr Leu Asp Leu Tyr
1               5                  10

<210> SEQ ID NO 56
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 56

Leu Val Val His Ile Arg Leu Asp Leu Tyr
1               5                  10

<210> SEQ ID NO 57
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members
<220> FEATURE:
<221> NAME/KEY: MOD_RES
<222> LOCATION: (1)..(1)
<223> OTHER INFORMATION: ACETYLATION

<400> SEQUENCE: 57

Leu Met Val Lys Ile Thr Leu Asp Leu Leu
1               5                  10

```
<210> SEQ ID NO 58
<211> LENGTH: 11
<212> TYPE: PRT
<213> ORGANISM: Artificial Sequence
<220> FEATURE:
<223> OTHER INFORMATION: structurally based on a fragment of the
      naturally occuring human and murine AF4 protein family members
<220> FEATURE:
<221> NAME/KEY: MOD_RES
<222> LOCATION: (1)..(1)
<223> OTHER INFORMATION: ACETYLATION

<400> SEQUENCE: 58

Val Leu Met Val Arg Ile Thr Leu Asp Leu Leu
1               5                   10

<210> SEQ ID NO 59
<211> LENGTH: 14
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 59

Leu Val Val Lys Ile Thr Leu Asp Pro Leu Thr Arg Ile Pro
1               5                   10

<210> SEQ ID NO 60
<211> LENGTH: 14
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 60

Leu Trp Val Lys Ile Asp Leu Thr Leu Leu Ser Arg Ile Pro
1               5                   10

<210> SEQ ID NO 61
<211> LENGTH: 14
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 61

Leu Ile Val Lys Ile Asp Leu Asn Leu Leu Thr Arg Ile Pro
1               5                   10

<210> SEQ ID NO 62
<211> LENGTH: 14
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 62

Leu Trp Val Lys Ile Asp Leu Asp Leu Leu Ser Arg Val Pro
1               5                   10

<210> SEQ ID NO 63
<211> LENGTH: 14
<212> TYPE: PRT
<213> ORGANISM: Artificial Sequence
<220> FEATURE:
```

-continued

```
<223> OTHER INFORMATION: structurally based on a fragment of the
      naturally occuring human and murine AF4 protein family members

<400> SEQUENCE: 63

Leu Trp Val Lys Ile Asp Leu Asp Leu Leu Ser Arg Val Pro
1               5                   10

<210> SEQ ID NO 64
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members
<220> FEATURE:
<221> NAME/KEY: MOD_RES
<222> LOCATION: (10)..(10)
<223> OTHER INFORMATION: METHYLATION

<400> SEQUENCE: 64

Leu Ile Val Arg Ile Thr Leu Asp Leu Leu
1               5                   10

<210> SEQ ID NO 65
<211> LENGTH: 20
<212> TYPE: PRT
<213> ORGANISM: Artificial Sequence
<220> FEATURE:
<223> OTHER INFORMATION: structurally based on a fragment of the
      naturally occuring human and murine AF4 protein family members
<220> FEATURE:
<221> NAME/KEY: DISULFID
<222> LOCATION: (1)..(20)

<400> SEQUENCE: 65

Leu Met Val Lys Ile Thr Leu Asp Leu Leu Leu Met Val Lys Ile Thr
1               5                   10                  15

Leu Asp Leu Leu
            20

<210> SEQ ID NO 66
<211> LENGTH: 14
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 66

Leu Met Val Lys Ile Asp Leu Asp Leu Leu Ser Arg Ile Pro
1               5                   10

<210> SEQ ID NO 67
<211> LENGTH: 11
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 67

Leu Ile Val Lys Val Thr Leu Asp Leu Leu Ser
1               5                   10

<210> SEQ ID NO 68
<211> LENGTH: 10
<212> TYPE: PRT
<213> ORGANISM: Artificial Sequence
```

```
<220> FEATURE:
<223> OTHER INFORMATION: structurally based on a fragment of the
      naturally occuring human and murine AF4 protein family members

<400> SEQUENCE: 68

Leu Leu Val His Ile Thr Leu Asp Leu Phe
1               5                   10

<210> SEQ ID NO 69
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 69

Leu Leu Val Arg Ile Thr Leu Asp Leu Phe
1               5                   10

<210> SEQ ID NO 70
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 70

Leu Trp Val Lys Ile Thr Leu Asp Ile Leu
1               5                   10

<210> SEQ ID NO 71
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 71

Leu Trp Val His Ile Thr Leu Asp Ile Leu
1               5                   10

<210> SEQ ID NO 72
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 72

Leu Trp Val Arg Ile Thr Leu Asp Ile Leu
1               5                   10

<210> SEQ ID NO 73
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 73

Leu Tyr Val Lys Ile Thr Leu Asp Leu Ile
1               5                   10
```

```
<210> SEQ ID NO 74
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 74

Leu Tyr Val His Ile Thr Leu Asp Leu Ile
1               5                   10

<210> SEQ ID NO 75
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 75

Leu Tyr Val Arg Ile Thr Leu Asp Leu Ile
1               5                   10

<210> SEQ ID NO 76
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 76

Leu Val Val Lys Ile Thr Leu Asp Trp Leu
1               5                   10

<210> SEQ ID NO 77
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 77

Leu Val Val His Ile Thr Leu Asp Trp Leu
1               5                   10

<210> SEQ ID NO 78
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 78

Leu Val Val Arg Ile Thr Leu Asp Trp Leu
1               5                   10

<210> SEQ ID NO 79
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members
```

-continued

```
<400> SEQUENCE: 79

Leu Val Val Lys Ile Thr Leu Asp Leu Trp
1               5                   10

<210> SEQ ID NO 80
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 80

Leu Val Val His Ile Thr Leu Asp Leu Trp
1               5                   10

<210> SEQ ID NO 81
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 81

Leu Val Val Arg Ile Thr Leu Asp Leu Trp
1               5                   10

<210> SEQ ID NO 82
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 82

Leu Val Val Lys Ile Thr Leu Asp Val Leu
1               5                   10

<210> SEQ ID NO 83
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 83

Leu Val Val His Ile Thr Leu Asp Val Leu
1               5                   10

<210> SEQ ID NO 84
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 84

Leu Val Val Arg Ile Thr Leu Asp Val Leu
1               5                   10

<210> SEQ ID NO 85
<211> LENGTH: 10
<212> TYPE: PRT
```

```
<213> ORGANISM: Artificial Sequence
<220> FEATURE:
<223> OTHER INFORMATION: structurally based on a fragment of the
      naturally occuring human and murine AF4 protein family members

<400> SEQUENCE: 85

Leu Val Val Lys Ile Thr Leu Asp Leu Val
1               5                   10

<210> SEQ ID NO 86
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 86

Leu Val Val His Ile Thr Leu Asp Leu Val
1               5                   10

<210> SEQ ID NO 87
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 87

Leu Met Val Arg Ile Thr Leu Asp Met Leu
1               5                   10

<210> SEQ ID NO 88
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 88

Leu Met Val His Ile Thr Leu Asp Met Leu
1               5                   10

<210> SEQ ID NO 89
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 89

Leu Phe Val Lys Ile Thr Leu Asp Leu Met
1               5                   10

<210> SEQ ID NO 90
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members
<220> FEATURE:
<221> NAME/KEY: BINDING
<222> LOCATION: (10)..(10)
<223> OTHER INFORMATION: 6-Diamidino-2-phenyl is attached to Met
```

```
<400> SEQUENCE: 90

Leu Phe Val His Ile Thr Leu Asp Leu Met
1               5                   10

<210> SEQ ID NO 91
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 91

Leu Phe Val Arg Ile Thr Leu Asp Leu Met
1               5                   10

<210> SEQ ID NO 92
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 92

Leu Val Val Lys Ile Thr Leu Asp Pro Leu
1               5                   10

<210> SEQ ID NO 93
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members
<220> FEATURE:
<221> NAME/KEY: MOD_RES
<222> LOCATION: (1)..(10)
<223> OTHER INFORMATION: ACETYLATION

<400> SEQUENCE: 93

Leu Trp Val Lys Ile Asp Leu Thr Leu Leu
1               5                   10

<210> SEQ ID NO 94
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 94

Leu Trp Val Lys Ile Asp Leu Asp Leu Leu
1               5                   10

<210> SEQ ID NO 95
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members
<220> FEATURE:
<221> NAME/KEY: MOD_RES
<222> LOCATION: (7)..(7)
<223> OTHER INFORMATION: METHYLATION

<400> SEQUENCE: 95
```

```
Leu Val Val Lys Ile Thr Leu Asp Leu Val
1               5                   10

<210> SEQ ID NO 96
<211> LENGTH: 14
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 96

Leu Trp Val Lys Ile Asp Leu Asp Leu Leu Ser Arg Ile Pro
1               5                   10

<210> SEQ ID NO 97
<211> LENGTH: 14
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 97

Leu Met Val Lys Ile Thr Leu Asp Leu Leu Ser Arg Ile Pro
1               5                   10

<210> SEQ ID NO 98
<211> LENGTH: 19
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 98

Lys Lys Lys Lys Lys Lys Arg Lys Val Leu Ile Val Arg Ile Asp Leu
1               5                   10                  15

Asp Leu Ser

<210> SEQ ID NO 99
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 99

Leu Ile Val Lys Ile Ala Leu Ala Leu Leu
1               5                   10

<210> SEQ ID NO 100
<211> LENGTH: 14
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 100

Leu Trp Val Lys Ile Thr Leu Asp Leu Leu Ser Arg Ile Pro
1               5                   10

<210> SEQ ID NO 101
<211> LENGTH: 16
```

```
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 101

Lys Lys Lys Arg Lys Val Leu Ile Val Arg Ile Asp Leu Asp Leu Ser
1               5                   10                  15

<210> SEQ ID NO 102
<211> LENGTH: 11
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 102

Cys Leu Ile Val Lys Ile Ala Leu Ala Leu Leu
1               5                   10

<210> SEQ ID NO 103
<211> LENGTH: 10
<212> TYPE: PRT
<213> ORGANISM: Human AF4 fragment

<400> SEQUENCE: 103

Leu Met Val Lys Ile Thr Leu Asp Leu Leu
1               5                   10

<210> SEQ ID NO 104
<211> LENGTH: 11
<212> TYPE: PRT
<213> ORGANISM: Artificial Sequence
<220> FEATURE:
<223> OTHER INFORMATION: a fragment of the naturally occuring human AF4
      protein

<400> SEQUENCE: 104

Leu Met Val Lys Ile Thr Leu Asp Leu Leu Ser
1               5                   10

<210> SEQ ID NO 105
<211> LENGTH: 15
<212> TYPE: PRT
<213> ORGANISM: Artificial Sequence
<220> FEATURE:
<223> OTHER INFORMATION: a cell penetration transport sequence

<400> SEQUENCE: 105

Arg Gln Ile Lys Trp Phe Gln Asn Arg Arg Met Lys Trp Lys Lys
1               5                   10                  15

<210> SEQ ID NO 106
<211> LENGTH: 14
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 106

Leu Trp Glu Lys Ser Asp Leu Asp Leu Leu Ser Arg Val Pro
1               5                   10

<210> SEQ ID NO 107
```

-continued

```
<211> LENGTH: 27
<212> TYPE: PRT
<213> ORGANISM: Human AF4 fragment

<400> SEQUENCE: 107

Leu Ser Pro Leu Arg Asp Thr Pro Pro Gln Ser Leu Met Val Lys
1               5                   10                  15

Ile Thr Leu Asp Leu Leu Ser Arg Ile Pro Gln
            20                  25

<210> SEQ ID NO 108
<211> LENGTH: 161
<212> TYPE: PRT
<213> ORGANISM: murine MPC3 fragment

<400> SEQUENCE: 108

Arg Lys Leu Asp Glu Thr Ser Ser Gly Thr Gly Lys Phe Pro Ala Gly
1               5                   10                  15

His Ser Val Ile Gln Leu Ala Arg Arg Gln Asp Ser Asp Leu Val Gln
            20                  25                  30

Tyr Gly Val Thr Ser Pro Ser Ser Ala Glu Ala Ser Ser Lys Leu Ala
        35                  40                  45

Val Asp Thr Phe Pro Ala Arg Val Ile Lys His Arg Ala Ala Phe Leu
50                  55                  60

Glu Ala Lys Gly Gln Gly Ala Leu Asp Pro Gly Gly Ala Arg Val Arg
65                  70                  75                  80

His Ser Ser Gly Thr Pro Ala Ser Val Gly Ser Leu Tyr Arg Asp Met
                85                  90                  95

Gly Ala Gln Gly Gly Arg Pro Ser Leu Ile Ala Arg Ile Pro Val Ala
            100                 105                 110

Arg Ile Leu Gly Asp Pro Glu Glu Ser Trp Ser Pro Ser Leu Thr
        115                 120                 125

Asn Leu Glu Lys Val Val Val Thr Asp Val Thr Ser Asn Phe Leu Thr
    130                 135                 140

Val Thr Ile Lys Glu Ser Asn Thr Asp Gln Gly Phe Phe Lys Glu Lys
145                 150                 155                 160

Arg

<210> SEQ ID NO 109
<211> LENGTH: 835
<212> TYPE: PRT
<213> ORGANISM: murine mBCoR

<400> SEQUENCE: 109

Asp Pro Lys Pro Phe Cys Val Gly Gly Ala Pro Pro Asn Met Asp Val
1               5                   10                  15

Thr Pro Ala Tyr Thr Lys Glu Gly Thr Asp Glu Ala Glu Ser Asn Asp
            20                  25                  30

Gly Lys Val Leu Lys Pro Lys Pro Ser Lys Leu Ala Lys Arg Ile Ala
        35                  40                  45

Asn Ser Ala Gly Tyr Val Gly Asp Arg Phe Lys Cys Val Thr Thr Glu
50                  55                  60

Leu Tyr Ala Asp Ser Ser Gln Leu Ser Arg Glu Gln Arg Ala Leu Gln
65                  70                  75                  80

Met Glu Gly Leu Gln Glu Asp Ser Ile Leu Cys Leu Pro Ala Ala Tyr
                85                  90                  95

Cys Glu Arg Ala Met Met Arg Phe Ser Glu Leu Glu Met Lys Glu Arg
```

-continued

```
                100                 105                 110
Glu Gly Ser His Pro Ala Thr Lys Asp Ser Glu Val Cys Lys Phe Ser
            115                 120                 125

Pro Ala Asp Trp Glu Arg Leu Lys Gly Asn Gln Glu Lys Lys Pro Lys
130                 135                 140

Ser Val Thr Leu Glu Glu Ala Ile Ala Asp Gln Asn Asp Ser Glu Arg
145                 150                 155                 160

Cys Glu Tyr Ser Thr Gly Asn Lys His Asp Leu Phe Glu Ala Pro Glu
                165                 170                 175

Asp Lys Asp Leu Pro Val Glu Lys Tyr Phe Leu Glu Arg Pro Pro Val
            180                 185                 190

Ser Glu Pro Pro Ser Asp Gln Gly Val Val Asp Thr Pro His Ser Pro
        195                 200                 205

Thr Leu Arg Leu Asp Arg Lys Arg Lys Leu Ser Gly Asp Ser Thr His
    210                 215                 220

Thr Glu Thr Ala Val Glu Glu Leu Ala Glu Asp Pro Leu Lys Ala Lys
225                 230                 235                 240

Arg Arg Arg Ile Ser Lys Asp Asp Trp Pro Glu Arg Glu Met Thr Asn
                245                 250                 255

Ser Ser Ser Asn His Leu Glu Asp Pro His Cys Asn Glu Leu Thr Asn
            260                 265                 270

Leu Lys Val Cys Ile Glu Leu Thr Gly Leu His Pro Lys Lys Gln Arg
        275                 280                 285

His Leu Leu His Leu Arg Glu Arg Trp Glu Gln Val Ser Ala Ala
    290                 295                 300

Glu Ser Lys Pro Gly Arg Gln Ser Arg Lys Glu Val Ala Gln Ala Val
305                 310                 315                 320

Gln Pro Glu Val Thr Ser Gln Gly Thr Asn Ile Thr Glu Glu Lys Pro
                325                 330                 335

Gly Arg Lys Lys Ala Glu Ala Lys Gly Asn Arg Gly Trp Ser Glu Glu
            340                 345                 350

Ser Leu Lys Ser Cys Asp Asn Glu Gln Gly Leu Pro Val Leu Ser Gly
        355                 360                 365

Ser Pro Pro Met Lys Ser Leu Ser Ser Thr Asn Ala Ser Gly Lys Lys
    370                 375                 380

Gln Thr Gln Pro Ser Cys Thr Pro Ala Ser Arg Leu Pro Ala Lys Gln
385                 390                 395                 400

Gln Lys Ile Lys Glu Ser Gln Lys Thr Asp Val Leu Cys Thr Gly Glu
                405                 410                 415

Asp Glu Asp Cys Gln Ala Ala Ser Pro Leu Gln Lys Tyr Thr Asp Asn
            420                 425                 430

Ile Glu Lys Pro Ser Gly Lys Arg Leu Cys Lys Thr Lys His Leu Ile
        435                 440                 445

Pro Gln Glu Ser Arg Arg Ser Leu Gln Ile Thr Gly Asp Tyr Tyr Val
    450                 455                 460

Glu Asn Thr Asp Thr Lys Met Thr Val Arg Arg Phe Arg Lys Arg Pro
465                 470                 475                 480

Glu Pro Ser Ser Asp Tyr Asp Leu Ser Pro Ala Lys Gln Glu Pro
                485                 490                 495

Lys Pro Phe Gly Arg Leu Gln Leu Leu Pro Ala Thr Gln Ala Thr
            500                 505                 510

Gln Leu Pro Arg Ser Asn Ser Pro Gln Glu Thr Thr Gln Ser Arg Pro
        515                 520                 525
```

```
Met Pro Pro Glu Ala Arg Arg Leu Ile Val Asn Lys Asn Ala Gly Glu
    530                 535                 540

Thr Leu Leu Gln Arg Ala Ala Arg Leu Gly Tyr Glu Val Val Leu
545                 550                 555                 560

Tyr Cys Leu Glu Asn Lys Val Cys Asp Val Asn His Arg Asp Asn Ala
                565                 570                 575

Gly Tyr Cys Ala Leu His Glu Ala Cys Ala Arg Gly Trp Leu Asn Ile
            580                 585                 590

Val Arg His Leu Leu Glu Tyr Gly Ala Asp Val Asn Cys Ser Ala Gln
        595                 600                 605

Asp Gly Thr Arg Pro Leu His Asp Ala Val Glu Asn Asp His Leu Glu
    610                 615                 620

Ile Val Arg Leu Leu Leu Ser Tyr Gly Ala Asp Pro Thr Leu Ala Thr
625                 630                 635                 640

Tyr Ser Gly Arg Thr Ile Met Lys Met Thr His Ser Glu Leu Met Glu
                645                 650                 655

Lys Phe Leu Thr Asp Tyr Leu Asn Asp Leu Gln Gly Arg Ser Glu Asp
            660                 665                 670

Asp Thr Ser Gly Ala Trp Glu Phe Tyr Gly Ser Ser Val Cys Glu Pro
        675                 680                 685

Asp Asp Glu Ser Gly Tyr Asp Val Leu Ala Asn Pro Pro Gly Pro Glu
    690                 695                 700

Asp Pro Asp Glu Glu Glu Asp Thr Tyr Ser Asp Leu Phe Glu Phe Glu
705                 710                 715                 720

Phe Ala Glu Ser Ser Leu Leu Pro Cys Tyr Asn Ile Gln Val Ser Val
                725                 730                 735

Ala Gln Gly Pro Arg Asn Trp Leu Leu Leu Ser Asp Val Leu Lys Lys
            740                 745                 750

Leu Lys Met Ser Ser Arg Ile Phe Arg Ser Asn Phe Pro Asn Leu Glu
        755                 760                 765

Ile Val Thr Ile Ala Glu Ala Glu Phe Tyr Arg Gln Val Ser Thr Ser
    770                 775                 780

Leu Leu Phe Ser Cys Pro Lys Asp Leu Glu Ala Phe Asn Pro Glu Ser
785                 790                 795                 800

Lys Glu Leu Leu Asp Leu Val Glu Phe Thr Asn Glu Leu Gln Thr Leu
                805                 810                 815

Leu Gly Ser Ser Val Glu Trp Leu His Pro Ser Asp Thr Gly His Glu
            820                 825                 830

Asn Tyr Trp
        835

<210> SEQ ID NO 110
<211> LENGTH: 13
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 110

Leu Trp Glu Lys Ser Asp Leu Asp Leu Leu Ser Arg Val
1               5                   10

<210> SEQ ID NO 111
<211> LENGTH: 12
<212> TYPE: PRT
```

```
<213> ORGANISM: Artificial Sequence
<220> FEATURE:
<223> OTHER INFORMATION: structurally based on a fragment of the
      naturally occuring human and murine AF4 protein family members

<400> SEQUENCE: 111

Leu Trp Val Lys Ile Asp Leu Asp Leu Leu Ser Arg
1               5                   10

<210> SEQ ID NO 112
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 112

Leu Trp Val Lys Ile Asp Leu Asp Leu Leu
1               5                   10

<210> SEQ ID NO 113
<211> LENGTH: 8
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 113

Trp Val Lys Ile Asp Leu Asp Leu
1               5

<210> SEQ ID NO 114
<211> LENGTH: 358
<212> TYPE: PRT
<213> ORGANISM: human AF9 fragment

<400> SEQUENCE: 114

Ser Arg Glu His Lys Ser Ala Phe Lys Glu Pro Ser Arg Asp His Asn
1               5                   10                  15

Lys Ser Ser Lys Glu Ser Ser Lys Lys Pro Lys Glu Asn Lys Pro Leu
            20                  25                  30

Lys Glu Glu Lys Ile Val Pro Lys Met Ala Phe Lys Glu Pro Lys Pro
        35                  40                  45

Met Ser Lys Glu Pro Lys Pro Asp Ser Asn Leu Leu Thr Ile Thr Ser
    50                  55                  60

Gly Gln Asp Lys Lys Ala Pro Ser Lys Arg Pro Pro Ile Ser Asp Ser
65                  70                  75                  80

Glu Glu Leu Ser Ala Lys Lys Arg Lys Lys Ser Ser Glu Ala Leu
                85                  90                  95

Phe Lys Ser Phe Ser Ser Ala Pro Pro Leu Ile Leu Thr Cys Ser Ala
                100                 105                 110

Asp Lys Lys Gln Ile Lys Asp Lys Ser His Val Lys Met Gly Lys Val
            115                 120                 125

Lys Ile Glu Ser Glu Thr Ser Glu Lys Lys Ser Thr Leu Pro Pro
        130                 135                 140

Phe Asp Asp Ile Val Asp Pro Asn Asp Ser Asp Val Glu Glu Asn Ile
145                 150                 155                 160

Ser Ser Lys Ser Asp Ser Glu Gln Pro Ser Pro Ala Ser Ser Ser Ser
                165                 170                 175
```

```
Ser Ser Ser Ser Ser Phe Thr Pro Ser Gln Thr Arg Gln Gln Gly Pro
            180                 185                 190

Leu Arg Ser Ile Met Lys Asp Leu His Ser Asp Asp Asn Glu Glu Glu
        195                 200                 205

Ser Asp Glu Val Glu Asp Asn Asp Asn Asp Ser Glu Met Glu Arg Pro
    210                 215                 220

Val Asn Arg Gly Gly Ser Arg Ser Arg Val Ser Leu Ser Asp Gly
225                 230                 235                 240

Ser Asp Ser Glu Ser Ser Ser Ala Ser Ser Pro Leu His His Glu Pro
                245                 250                 255

Pro Pro Pro Leu Leu Lys Thr Asn Asn Asn Gln Ile Leu Glu Val Lys
            260                 265                 270

Ser Pro Ile Lys Gln Ser Lys Ser Asp Lys Gln Ile Lys Asn Gly Glu
        275                 280                 285

Cys Asp Lys Ala Tyr Leu Asp Glu Leu Val Glu Leu His Arg Arg Leu
    290                 295                 300

Met Thr Leu Arg Glu Arg His Ile Leu Gln Gln Ile Val Asn Leu Ile
305                 310                 315                 320

Glu Glu Thr Gly His Phe His Ile Thr Asn Thr Thr Phe Asp Phe Asp
                325                 330                 335

Leu Cys Ser Leu Asp Lys Thr Thr Val Arg Lys Leu Gln Ser Tyr Leu
            340                 345                 350

Glu Thr Ser Gly Thr Ser
            355

<210> SEQ ID NO 115
<211> LENGTH: 189
<212> TYPE: PRT
<213> ORGANISM: mouse AF4

<400> SEQUENCE: 115

Gln Thr Ser Lys Asp Arg Pro Lys Val Lys Thr Lys Gly Arg Pro Arg
1               5                   10                  15

Ala Val Gly Ser Arg Glu Pro Lys Pro Glu Val Pro Ala Pro Thr Pro
            20                  25                  30

Gln Ala Ala Val Pro Arg Pro Lys Pro Pro Val Pro Thr Pro Ser Glu
        35                  40                  45

Lys Arg Lys His Lys Ser Ser Thr Ala Pro Ser Lys Ala Pro Ser Ala
    50                  55                  60

Pro Gln Pro Pro Lys Asp Ser Ala Gly Asp Arg Asn Pro Glu His Ser
65                  70                  75                  80

Ala Leu Val Ser Leu Thr Gln Ser Gln Gly Pro Ser His Ser Ser Arg
                85                  90                  95

Gly Ser Ser Gly Ser Val Arg Thr Ser Gly Cys Arg Gln Ala Val Ile
            100                 105                 110

Ala Gln Gly Asp Gly Cys Lys Asp Lys Leu Leu Leu Pro Leu Arg Asp
        115                 120                 125

Thr Lys Leu Leu Ser Pro Leu Arg Asp Ser Pro Pro Thr Ser Leu
    130                 135                 140

Val Val Lys Ile Thr Leu Asp Leu Leu Thr Arg Ile Pro Gln Pro Leu
145                 150                 155                 160

Gly Lys Gly Ser Arg Pro Arg Lys Ala Glu Asp Lys Gln Leu Ser Ala
                165                 170                 175

Gly Lys Lys Gln Asp Ser Glu Thr Lys Ser Cys Asp Ser
            180                 185
```

```
<210> SEQ ID NO 116
<211> LENGTH: 5
<212> TYPE: PRT
<213> ORGANISM: Artificial Sequence
<220> FEATURE:
<223> OTHER INFORMATION: structurally based on a fragment of the
      naturally occuring human and murine AF4 protein family members
<220> FEATURE:
<221> NAME/KEY: MISC_FEATURE
<222> LOCATION: (1)..(1)
<223> OTHER INFORMATION: any of the amino acids in position 1 can be
      selectively modified by any of the R1 group of amino acids or
      compounds
<220> FEATURE:
<221> NAME/KEY: MISC_FEATURE
<222> LOCATION: (1)..(1)
<223> OTHER INFORMATION: is a hydrophobic amino acid
<220> FEATURE:
<221> NAME/KEY: MISC_FEATURE
<222> LOCATION: (3)..(3)
<223> OTHER INFORMATION: is a positively charged amino acid
<220> FEATURE:
<221> NAME/KEY: MISC_FEATURE
<222> LOCATION: (5)..(5)
<223> OTHER INFORMATION: can be any amino acid
<220> FEATURE:
<221> NAME/KEY: MISC_FEATURE
<222> LOCATION: (5)..(5)
<223> OTHER INFORMATION: any of the amino acids in position 5 can be
      selectively modified by any of the R2 group of amino acids or
      compounds

<400> SEQUENCE: 116

Xaa Val Xaa Ile Xaa
1               5

<210> SEQ ID NO 117
<211> LENGTH: 10
<212> TYPE: PRT
<213> ORGANISM: Artificial Sequence
<220> FEATURE:
<223> OTHER INFORMATION: structurally based on a fragment of the
      naturally occuring human and murine AF4 protein family members

<400> SEQUENCE: 117

Leu Ile Val Lys Ile Ala Leu Ala Leu Leu
1               5                   10

<210> SEQ ID NO 118
<211> LENGTH: 4
<212> TYPE: PRT
<213> ORGANISM: Artificial Sequence
<220> FEATURE:
<223> OTHER INFORMATION: spacer

<400> SEQUENCE: 118

Lys Pro Ala Gly
1
```